(12) United States Patent
Procyshyn et al.

(10) Patent No.: US 10,067,151 B2
(45) Date of Patent: Sep. 4, 2018

(54) METHOD FOR PROTECTING AND UNPROTECTING THE FLUID PATH IN A CONTROLLED ENVIRONMENT ENCLOSURE

(71) Applicants: Christopher Procyshyn, Surrey (CA); Marcin Cichy, Surrey (CA)

(72) Inventors: Christopher Procyshyn, Surrey (CA); Marcin Cichy, Surrey (CA)

(73) Assignee: VANRX PHARMASYSTEMS INC., Burnaby (CA)

( * ) Notice: Subject to any disclaimer, the term of this patent is extended or adjusted under 35 U.S.C. 154(b) by 0 days.

(21) Appl. No.: 15/375,019

(22) Filed: Dec. 9, 2016

(65) Prior Publication Data

US 2017/0248626 A1   Aug. 31, 2017

Related U.S. Application Data

(60) Provisional application No. 62/265,938, filed on Dec. 10, 2015.

(51) Int. Cl.
*G01N 35/10*    (2006.01)
*A61J 1/14*     (2006.01)
(Continued)

(52) U.S. Cl.
CPC ............ *G01N 35/10* (2013.01); *A61J 1/14* (2013.01); *A61J 1/20* (2013.01); *B01L 3/02* (2013.01);
(Continued)

(58) Field of Classification Search
CPC ............. B01L 3/02; B01L 2200/026; B01L 2200/0689; B01L 2200/141;
(Continued)

(56) References Cited

U.S. PATENT DOCUMENTS 4,376,634 A    3/1983   Prior et al.
4,976,699 A    12/1990  Gold
(Continued)

FOREIGN PATENT DOCUMENTS

WO    2009123911    10/2009

OTHER PUBLICATIONS

International Search Report by International Searching Authority (International Application No. PCT/IB2016/001958), dated May 19, 2017.
(Continued)

*Primary Examiner* — Timothy C Cleveland
(74) *Attorney, Agent, or Firm* — Kevin R. Erdman; Brannon Sowers & Cracraft PC

(57) ABSTRACT

A controlled environment enclosure comprises a robotic arm manipulation system used to protect and unprotect a fluid path and a swab within the controlled environment enclosure. The apparatus allows the fluid path to be protected against dangerous decontamination vapors and chemicals before the controlled environment enclosure is decontaminated. The apparatus allows the fluid path to be unprotected without the use of gloves or other means that degrade the integrity of the controlled environment enclosure when decontamination is completed. The apparatus and method allow for the protecting, unprotecting and decontaminating sequences to be automated. In some embodiments the fluid path comprises a fill needle that can removably and aseptically be sealed with a disposable monolithic injection molded polymeric fill needle sheath. The apparatus and method further allow for the use of a swab disposed in a swab holder that is aseptically and removably sealable to a swab cap to protect the swab against decontamination vapors.

12 Claims, 19 Drawing Sheets

(51) Int. Cl.
| | |
|---|---|
| *A61J 1/20* | (2006.01) |
| *B65B 55/12* | (2006.01) |
| *B65B 3/04* | (2006.01) |
| *B01L 3/02* | (2006.01) |
| *G01N 35/00* | (2006.01) |
| *B65B 3/00* | (2006.01) |

(52) U.S. Cl.
CPC ............... *B65B 3/003* (2013.01); *B65B 3/04* (2013.01); *B65B 55/12* (2013.01); *G01N 35/00029* (2013.01); *G01N 35/0099* (2013.01); *B01L 2200/026* (2013.01); *B01L 2200/0689* (2013.01); *B01L 2200/141* (2013.01); *B01L 2300/0609* (2013.01); *G01N 2035/00148* (2013.01); *G01N 2035/00277* (2013.01)

(58) Field of Classification Search
CPC ...... B01L 2300/0609; G01N 35/00029; G01N 35/0099; G01N 35/10; G01N 2035/00148; G01N 2035/00277
See application file for complete search history.

(56) References Cited

U.S. PATENT DOCUMENTS

| | | |
|---|---|---|
| 5,341,854 A | 8/1994 | Zezulka et al. |
| 6,116,670 A | 9/2000 | Palone et al. |
| 8,372,353 B2 | 2/2013 | Lee et al. |

OTHER PUBLICATIONS

Written Opinion by International Searching Authority (International Application No. PCT/IB2016/001958), dated May 19, 2017.

METHOD FOR PROTECTING AND UNPROTECTING THE FLUID PATH IN A CONTROLLED ENVIRONMENT ENCLOSURE

CROSS-REFERENCE TO RELATED APPLICATIONS

The subject matter of this application relates to that disclosed in U.S. patent application Ser. No. 14/890,223 which is a US National Phase Entry of PCT Application PCT/US2012/047765, filed Jul. 20, 2012, which claims priority to provisional application 61/510,780 filed Jul. 22, 2011. All of these applications are herein incorporated by reference.

TECHNICAL FIELD

This document relates generally to apparatus and methods for use in handling materials in controlled environment enclosures, including apparatus and methods for aseptically filling pharmaceutical containers using a fluid path that is protected and unprotected.

BACKGROUND

Controlled environment enclosures are known in the art. Such enclosures are used, for example, for containment of hazardous materials. In other examples controlled environment enclosures are used to provide controlled environments with limited numbers of particulates.

In the art controlled environment enclosures are typically fitted with ports for transfer of materials in and out of the enclosure and the ports are fitted with gloves for manual manipulation of equipment, parts or materials inside the enclosure. Such gloves are subject to significant risk of puncture.

In some examples known in the art the controlled environment enclosure is also used to limit exposure to viable particulates. Such controlled environment enclosures may be required for aseptic processing of cell cultures and for the manufacture of pharmaceutical products, medical devices, food or food ingredients. In these cases it is a requirement that the controlled environment enclosure be decontaminated. This may be done thermally using steam or chemically using chemical agents. Suitable chemical agents known in the art include hydrogen peroxide, ozone, beta-propiolactone, aziridine, formaldehyde, chlorine dioxide, ethylene oxide, propylene oxide, and peracetic acid. In most cases the decontamination and sterilization operations have to be preceded by a cleaning process. Such cleaning processes have the function of removing major contamination by simple mechanical and chemical action.

In some examples in the prior art the controlled environment also contains automated equipment. Such automated equipment includes machines for filling of vials. The automated equipment located in the controlled environment is typically of such a size and complexity that it cannot be operated fully automatically without human intervention. Such human intervention typically requires the use of gloves with the associated risk of puncture.

Fluid paths within the controlled environment enclosures may be made from flexible tubing materials and can therefore have significant gas permeability. Gases that naturally occur in air, such as oxygen and carbon dioxide, as well as chemical decontamination agents, are known to diffuse into these tubing materials. Accumulation of these agents in flexible tubing and subsequent delayed release can be a major contamination problem during operation. This applies in particular to products or solutions that are sensitive to exposure to alkylating agents, oxidizers, radicals or carbon dioxide. A typical example of human intervention involving the use of gloves is the installation of the fluid path or multiple fluid paths after the completion of decontamination.

In view of the above there remains a need for controlled environments that do not require human intervention via the use of gloves.

SUMMARY OF THE INVENTION

In one aspect of the invention there is provided a method for installing a fluid path within a controlled environment enclosure comprising, protecting the fluid path against an environment external to the fluid path; introducing the fluid path into the controlled environment enclosure; decontaminating the controlled environment enclosure; and mechanically unprotecting the fluid path within the controlled environment enclosure. The mechanically unprotecting can be by a robotic arm manipulation system. The decontaminating the controlled environment enclosure is automatically done after the introducing the fluid path into the controlled environment enclosure. The unprotecting is automatically done after the decontaminating the controlled environment enclosure.

In one aspect of the invention there is provided a method for transferring within a controlled environment enclosure a fluid along a fluid path to a destination within the controlled environment enclosure, comprising protecting the fluid path against an environment external to the fluid path; introducing the fluid path into the controlled environment enclosure; decontaminating the controlled environment enclosure; mechanically unprotecting the fluid path within the controlled environment enclosure; and transferring the fluid to the destination along the fluid path. The mechanically unprotecting can be by a robotic arm manipulation system. The fluid path can comprise a pre-sterilized tube. The method can further comprise filtering the fluid in the fluid path and the filtering can be sterile filtering. The destination can be at least one of a culture of cells, a culture of tissue, an enzyme solution, a suspension of immobilized enzymes, a mix of active ingredients, and an excipient. The fluid can be an aseptic fluid. The controlled environment enclosure can be an isolator. The destination can be microwell plates or containers for pharmaceutical products.

In one aspect of the invention there is provided a method for uninstalling a fluid path from a controlled environment enclosure, comprising mechanically protecting the fluid path within the controlled environment enclosure; decontaminating the controlled environment enclosure; opening the controlled environment enclosure; and removing the fluid path from the controlled environment enclosure. The mechanically protecting can be by a robotic arm manipulation system. The decontaminating the controlled environment enclosure can be done automatically after the protecting the fluid path. The opening the controlled environment enclosure can be done automatically after the decontaminating the controlled environment enclosure.

In one aspect of the invention there is provided a method for decontaminating a controlled environment enclosure having a fluid path, the method comprising mechanically protecting by a robotic action the fluid path within the controlled environment enclosure; decontaminating the controlled environment enclosure; and opening and closing the controlled environment enclosure. The opening and closing the controlled environment enclosure can be done before or after the decontaminating the controlled environment enclosure. The mechanically protecting can be by a robotic arm manipulation system. The decontaminating the controlled environment enclosure can be done automatically after the mechanically protecting the fluid path.

In one aspect of the invention there is provided an apparatus for protection and unprotection of a fluid path within a controlled environment enclosure that includes a fluid path terminated by a fill needle with removable sheath, and a remotely operated manipulation system for protection and/or unprotection of the fluid path. The remotely operated manipulation system can include a robotic arm manipulation system. The apparatus can further include a tamper-evident device positioned to reveal a breach of seal between the sheath and the fill needle. The apparatus can further include a removal station that includes a surface operative to interact with part of the sheath. The remotely operated manipulation system can include a robot end tool including at least one surface that is shaped to hold the fill needle. The fluid path can be a pre-sterilized unit.

In one aspect of the invention there is provided an apparatus for installing a fluid path within a controlled environment enclosure that includes means for conveying the fluid, and remotely operated means for protecting and/or unprotecting the means for conveying the fluid.

The inventors envision that compact and well-designed automated equipment can be operated inside closed controlled environments without the use of any gloves, eliminating thereby the risk of leaky gloves. The invention provides a method of installing a fluid path inside a controlled environment enclosure without the use of gloves. This requires the fluid path to be protected during the decontamination process and to be unprotected prior to the use of the fluid path. Furthermore the fluid path can be automatically closed after use.

The closed fluid path can be re-opened and re-used at a later time. This can be useful for continuing the use of the fluid path after unplanned events that require breaking of the integrity of the enclosed controlled environment. Additionally the closing of the fluid path can be particularly useful in situations where the fluid path has been in use for transfer of hazardous substances. After closing of the fluid path, the enclosed environment can be cleaned and decontaminated; after which the fluid path can be removed.

In a first aspect of the invention a fluid handling assembly is provided for automatically carrying out a fluid handling process in an aseptic environment, the assembly comprising a first sheath portion including an implement portion disposed within the first sheath portion for use in the process, a first locking mechanism portion, and a first sealing portion; a second sheath portion including a second locking mechanism portion configured to mate with positive detent with the first locking mechanism portion, and a second sealing portion disposed to aseptically seal with the first sealing portion when the first and second locking mechanism portions are mutually mated, wherein the first and second sheath portions define a sealed cavity that aseptically encapsulates the implement portion when the first and second locking mechanism portions are mutually mated. The assembly may be a fill assembly and the implement portion comprises a proximal dispensing portion of a fill needle, the fill needle including a fluid conduit that extends through the first sheath portion to a distal fluid supply end so that, when the first and second locking mechanism portions are mutually mated, the proximal dispensing portion of the fill needle is located inside the cavity and the distal fluid supply end of the fluid conduit is located outside the cavity. The fluid conduit may include a flexible tube in fluid communication with the proximal dispensing portion of the fill needle. The assembly may be a swab assembly with the implement portion comprising a swab disposed inside the cavity when the first and second locking mechanism portions are mutually mated.

The assembly may further comprise a controlled environment enclosure configured to aseptically isolate the process and hold the fluid handling assembly, and an articulated robot arm disposed within the enclosure to manipulate the fluid handling assembly. The first and second sheath portions may respectively comprise first and second engagement portions. The assembly may further comprise a robotic arm endpiece for the robotic arm, the endpiece configured to bear the first sheath portion by engagement with positive detent with the first engagement portion and a holding station comprising a first holding fixture to hold the second sheath portion, the fixture configured for engaging with the second engagement portion. The holding station may comprise angled fingers disposed to engage with the second engagement portion of the second sheath portion to release the first sheath portion from the second sheath portion. The holding station may comprise a second holding fixture configured to suspend the mutually engaged first and second sheath portions.

The first and second sheath portions may be separate injection molded parts and wherein the locking mechanism portions include at least one integrally molded spring member. The assembly may further include a tamper indicator that is mechanically linked to one of the locking mechanism portions and includes a portion that is constructed to irreversibly tear in response to the mechanical separation of the first and second sealing surfaces.

The first and second locking mechanism portions may be configured to mutually mate when the first and second locking mechanism portions are moved towards each other along a locking axis. The first sheath portion may further include a first bearing surface positioned at least generally normal to the locking axis, and the second sheath portion may further include a second bearing surface positioned at least generally normal to the locking axis and facing the first bearing surface.

In a further aspect a method is provided for automatically carrying out a fluid handling process in controlled environment enclosure, the method comprising providing a first implement inside a first sealed sheath, the first sheath sealed by a detent-based sealing mechanism on the first sheath that keeps the first sheath aseptically sealed around the first implement; placing the first sheath in the controlled environment enclosure; decontaminating the controlled environment enclosure around the first sheath after the step of placing; actuating the sealing mechanism to open the first sheath, and carrying out at least one step in the fluid handing process with the implement in the controlled environment enclosure. The step of providing may include providing a fill needle and wherein the step of carrying out includes carrying out a fill operation. The step of decontaminating may take place before the step of carrying out a fill operation, further including a step of again actuating the sealing mechanism to seal the first sheath.

The method may further include an additional step of decontaminating the controlled environment chamber after the steps of carrying out a fill operation and again actuating the sealing mechanism. The method may yet further include providing a swab inside a second sealed sheath, providing a second detent-based sealing mechanism on the second sheath that keeps the second sheath sealed around the swab, placing the second sheath in the controlled environment enclosure, wherein the step of decontaminating decontaminates the outside of the second sheath, and swabbing the fill needle after the step of carrying out a fill operation.

The method may further include the steps of removing the first implement and the first sheath from the controlled environment enclosure, discarding the first implement and the first sheath, providing a second implement inside a second sealed sheath, providing a second detent-based sealing mechanism on the second sheath that keeps the second sheath sealed around the second implement, placing the second sheath in the controlled environment enclosure, decontaminating the controlled environment enclosure around the second sheath, and carrying out at least one step in another run of the fluid handing process with the implement in the aseptic environment.

The steps of actuating the first sealing mechanism and carrying out the filling operation a may be performed at least in part by a robotic arm disposed within the controlled environment enclosure. The method may further include the step of providing a pre-sterilized tube aseptically sealed to the fill needle. The step of carrying out a fill operation may include transferring fluid to at least one of a culture of cells, a culture of tissue, an enzyme solution, a suspension of immobilized enzymes, a mix of active ingredients, and an excipient. The step of carrying out a fill operation may include transferring fluid to at least one of microwell plates and containers for pharmaceutical products.

In a further aspect, a method is provided for automatically carrying out a fluid handling process in controlled environment enclosure, comprising: providing a plurality of disposable implements each aseptically sealed inside one of a plurality of disposable sheaths, placing a first of the plurality of sealed sheaths that contains a first of the plurality of implements in the controlled environment enclosure, decontaminating the controlled environment enclosure around the first sheath after the step of placing the first sheath, opening the first sheath, carrying out at least one step in the fluid handing process with the first implement in the controlled environment enclosure, removing the first sheath and the first implement from the controlled environment enclosure, discarding the first implement and the first sheath, placing a second of the plurality of sealed sheaths that contains a second of the plurality of implements in the controlled environment enclosure, decontaminating the controlled environment enclosure around the second sheath after the step of placing the second sheath, opening the second sheath, carrying out at least one step in another run of the fluid handing process with the second implement in the controlled environment, and repeating the steps of placing, decontaminating, opening, removing, and discarding for successive further ones of the plurality of disposable implements and corresponding ones of the plurality of disposable sheaths. The step of providing may provide a plurality of disposable implements that each include an intact tamper indicator. The steps of placing the first, second, and further sheaths may each include placing the intact tamper indicator for the sheath being placed, and the steps of opening the first, second, and further sheaths may each include disrupting the tamper indicator for the sheath being opened.

In a further aspect, a fluid handling assembly is provided for automatically carrying out a fluid handling process in an aseptic environment, comprising: a first sheath portion including an implement portion disposed within the first sheath portion for use in the process, a first locking mechanism portion, a first sealing portion, and a first bearing surface positioned at least generally normal to a locking axis; a second sheath portion including: a second locking mechanism portion configured to mate with the first locking mechanism portion when the first and second locking mechanism portions are moved towards each other along the locking axis, a second sealing portion disposed to aseptically seal with the first sealing portion when the first and second locking mechanism portions are mutually mated, and a second bearing surface positioned at least generally normal to the locking axis and facing toward the first bearing surface, wherein the first and second sheath portions define a sealed cavity that aseptically encapsulates the implement portion when the first and second locking mechanism portions are mutually mated.

In a further aspect, a fluid handling assembly is provided for automatically carrying out a fluid handling process in an aseptic environment, comprising: a first sheath portion including a swab disposed within the first sheath portion for use in the process, and a first sealing portion; and a second sheath portion including a second sealing portion disposed to aseptically seal with the first sealing portion, wherein the first and second sheath portions define a sealed cavity that aseptically encapsulates the swab when the first and second sealing portions are mutually mated.

In a further aspect, a method is provided for automatically carrying out a fluid handling process in controlled environment enclosure, comprising: providing a swab inside a first aseptically sealed sheath, placing the first sheath in the controlled environment enclosure, decontaminating the controlled environment enclosure around the first sheath after the step of placing, opening the first sheath, and swabbing an implement used in the fluid handing process with the swab in the controlled environment enclosure.

Other features, elements, steps, characteristics and advantages of the present invention will become more apparent from the following detailed description of preferred embodiments of the present invention.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9a and FIG. 9b show isometric and sectional views respectively of a combination of a fill needle and a fill needle sheath, while

DETAILED DESCRIPTION

Figure 1:
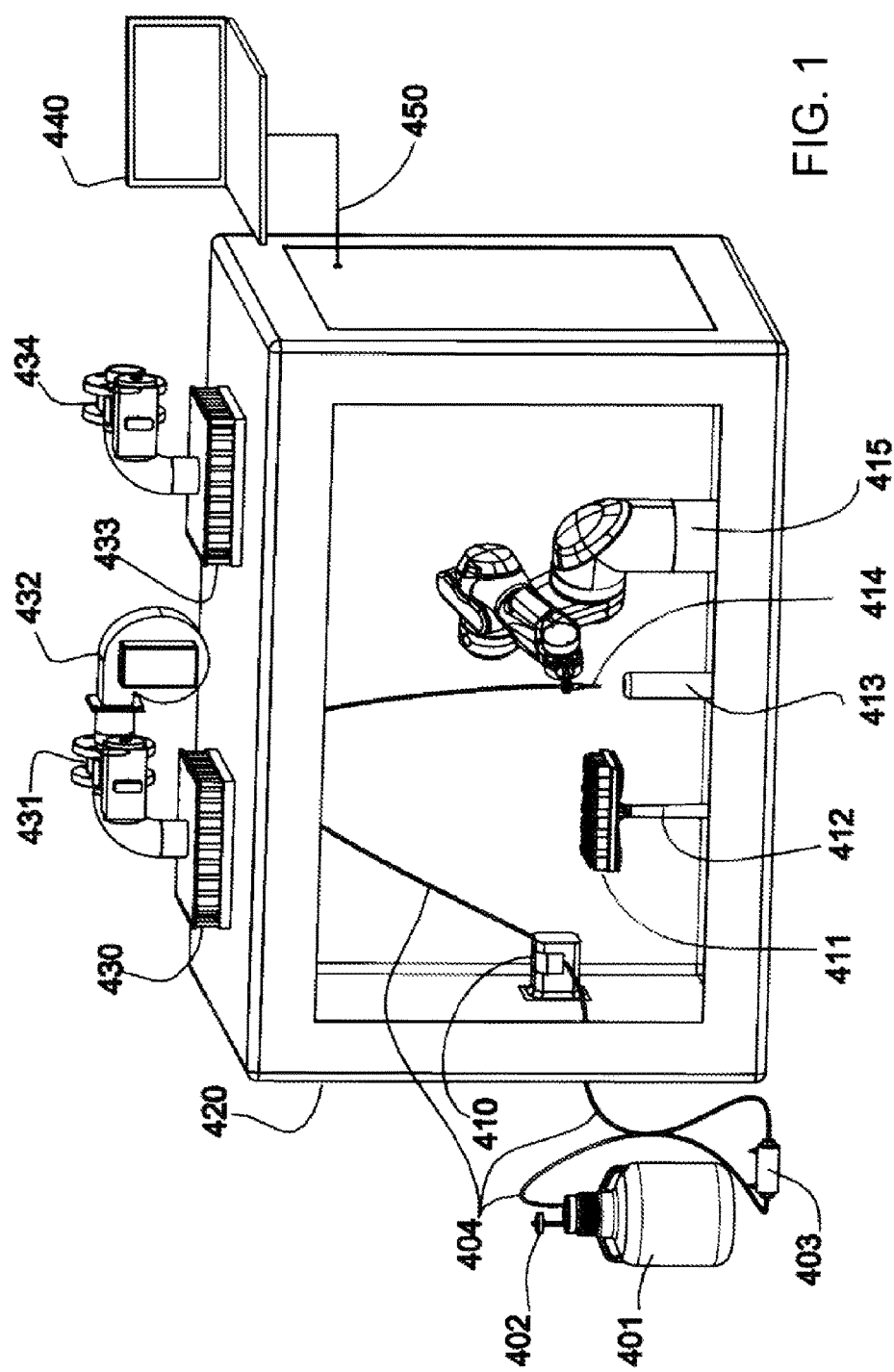
FIG. 1 shows an apparatus for the protecting and unprotecting of a fluid path in a controlled environment enclosure.

FIG. 1 shows an embodiment of an apparatus for protecting and unprotecting of a fluid path 404 in a controlled environment enclosure 420. The term "fluid" as used herein denotes any liquid, gas, liquid-gas mixtures and any mixture of solids in liquid that has fluid attributes, such as flowability or having appreciable fluidity at ambient temperature and pressure, including, without limitation, a dispersion of a solid or solids in a liquid, an emulsion, a slurry, a microemulsion, colloidal suspension, a suspension, a suspension of liposomes, and a suspension of micelles or the like. The term "fluid path" as used herein denotes any single channel or multi channel tubing, rigid or flexible, for transporting a fluid.

A fluid path 404 starts at a container 401. The term "container" as used herein denotes any vessel suitable to hold a fluid, including without limitation any vial, syringe, ampoule, carpule, bottle, flask, beaker, bag, well in multi-well plates, or tube. The container 401 is fitted with an air filter 402. The container 401 can be equipped with optional sensors (not shown) to measure volume, weight of fluid, or other parameters. In some embodiments there can be multiple containers connected in parallel or in series with one another. Along the fluid path 404 there can be optional measuring devices (not shown) that measure properties, including without limitation any one or more of pressure, flow, temperature, density and conductivity. The fluid path 404 can be fitted with a filter element 403. The filter element 403 can be selected to be suitable for sterile filtration of fluids.

In FIG. 1 the fluid path 404 comprises flexible tubing 405 and enters the controlled environment enclosure 420 via a sealed opening (not shown). The sealing can be, for example, via the use of a suitable aseptically sealing flange (not shown), which may seal by means of, for example without limitation, an aseptic tri-clamp. The container 401 and air filter 402 can be located outside the controlled environment enclosure 420, as shown in FIG. 1. In other embodiments of the invention the container 401 and air filter 402 can be located inside the controlled environment enclosure 420.

Controlled environment enclosure 420 is equipped with an inlet filter 430, an inlet valve 431, a blower 432, an outlet filter 433 and an outlet valve 434. The characteristics of blower 432, inlet filter 430 and outlet filter 433 are chosen to yield a controlled environment inside controlled environment enclosure 420. As understood by those skilled in the art, various other filter and blower arrangements are possible to establish a controlled environment inside controlled environment enclosure 420. A suitable controlled environment can be obtained, for example without limitation, by means of any one or more of turbulent airflow, horizontal unidirectional airflow and vertical unidirectional airflow.

The fluid from container 401 can be transferred through the fluid path 404 by a number of different mechanisms, including without limitation a peristaltic pump 410 as shown in FIG. 1, a difference in pressure between the container 401 and the controlled environment enclosure 420, a difference in static height of the container 401 and the end of the fluid path 404, a gear pump, a lobe pump, a membrane pump, a piston pump, or a syringe pump. In FIG. 1, pump 410 is shown disposed inside controlled environment enclosure 420. In other embodiments, pump 410 may be disposed outside controlled environment enclosure 420.

The flexible tubing 405 of the fluid path 404 can terminate with an end piece 414. A suitable end piece can be, for example without limitation, a fill needle, a pipette dispensing system, a syringe dispensing system, a valve dispensing system, quick connectors, aseptic connectors, dispense tips and a needle for piercing of elastomers. In FIG. 1 the end piece 414 is selected to be a fill needle.

The end piece 414 can be manipulated inside the controlled environment enclosure 420 by mechanical means, for example, a robotic arm manipulation system 415. A suitable robotic arm manipulation system 415 may be an articulated robotic arm. Suitable robotic arm manipulation systems for mechanically manipulating end piece 414 include, but are not limited to, 6-axis robotic arms, Selective Compliant Articulated Robot Arm (SCARA) systems, r-theta robots, or combinations of linear actuators and rotary actuators.

Fluids are transferred along the fluid path 404 to a destination, which can be containers such as the tray with vials 411 located on pedestal 412 in FIG. 1. The destination may be microwell plates for pharmaceutical products.

The fluid path 404 may be employed for a variety of purposes including without limitation the filling of empty containers, washing and rinsing of containers, adding fluid to containers with a freeze dried powder, adding fluids to containers containing excipients and/or active ingredients, adding medium to cells, tissue or microbes, inoculating cells or microbes, adding substrate to enzyme solutions or suspensions of immobilized enzymes, adding gases such as argon or nitrogen to create an inert head space in containers, adding gases such as nitrogen, air or carbon dioxide to cells and removing fluids out of containers by suction. The term "excipient" as used herein denotes an inert substance used as a diluent or vehicle for a drug.

Fluid path 404 may in some applications be required for aseptic transfer of fluids. In such a case fluid path 404 can be pre-sterilized before installation in the controlled environment enclosure 420. The aseptic part of the fluid path 404 can start with container 401 or with filter 403. Installation of the aseptic fluid path 404 requires sealing of the end piece 414.

Figure 4:
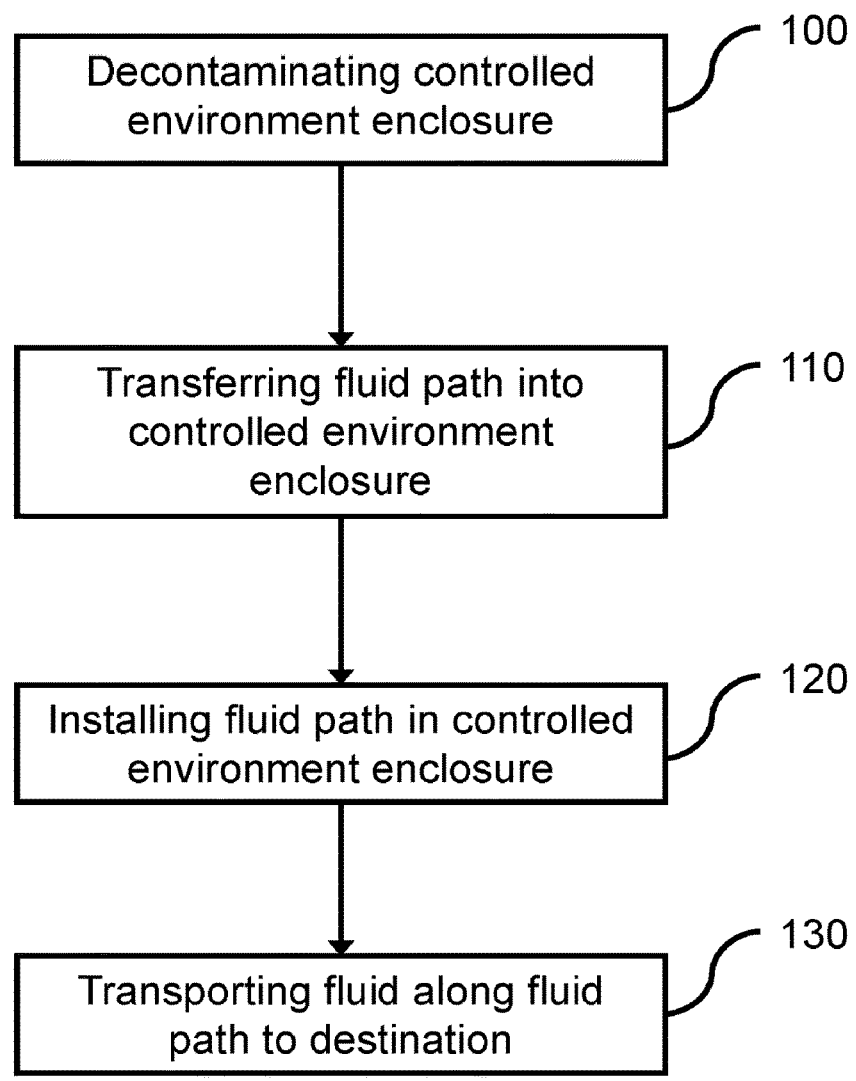
FIG. 4 is a flow chart for the typical prior art method.

FIG. 4 is a flowchart showing the prior art method for installing a fluid path in a prior art controlled environment enclosure. The prior art method requires the steps in sequence of decontaminating (100) the prior art controlled environment enclosure; transferring (110) the fluid path into the prior art controlled environment enclosure; and installing (120) by hand the fluid path in the prior art controlled environment enclosure, before using (130) the fluid path for the purpose for which it is intended.

Figure 5:
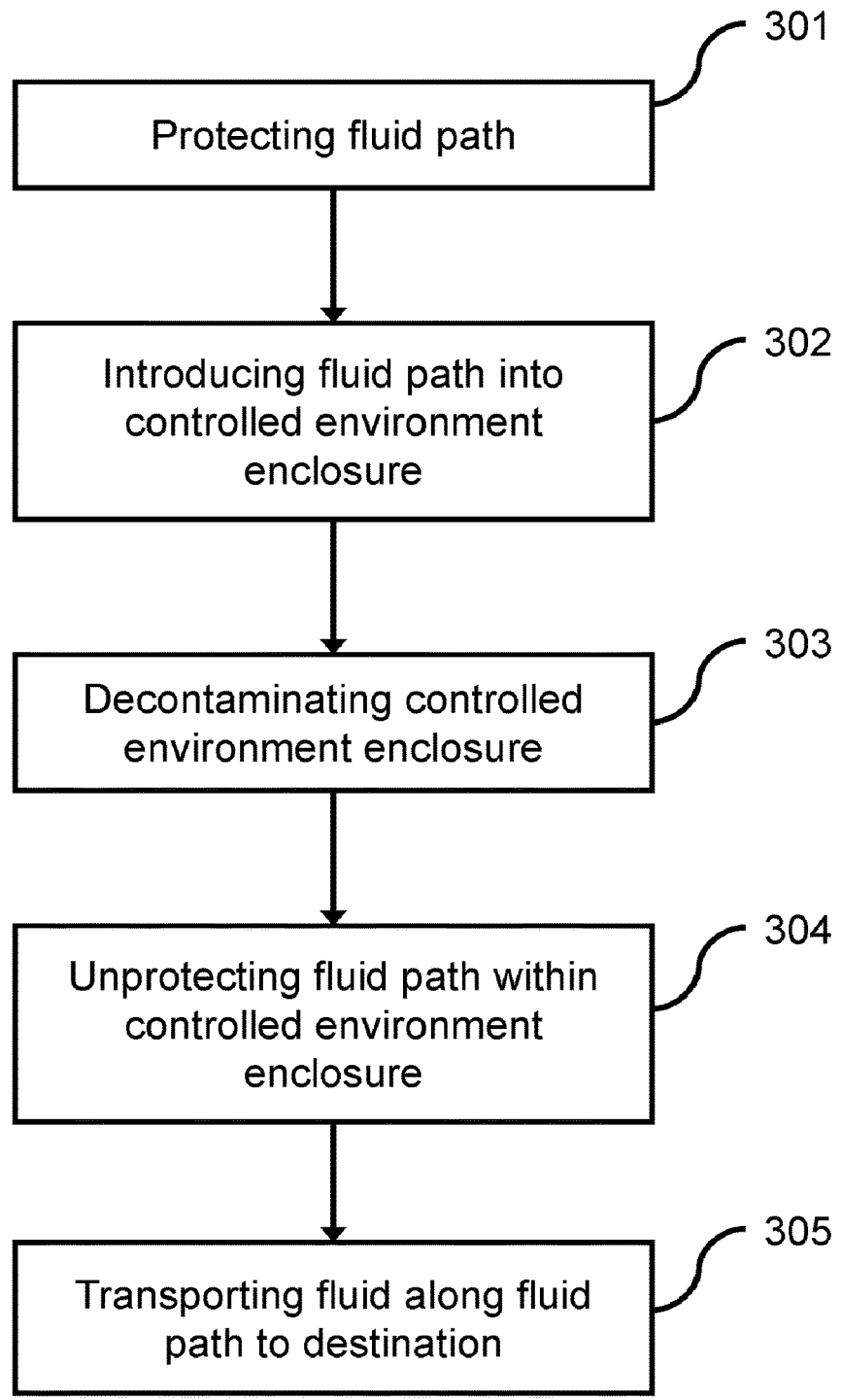
FIG. 5 shows a method flow chart of an aspect of the invention.

In an aspect of the invention there is provided a method for installing a fluid path 404 in the controlled environment enclosure 420. Referring to the apparatus of FIG. 1 and the flow chart of FIG. 5, the method comprises protecting (301) the fluid path 404 against an environment external to the fluid path 404, introducing (302) the fluid path 404 into the controlled environment enclosure 420, decontaminating (303) the controlled environment enclosure 420, and mechanically unprotecting (304) the fluid path 404. In its unprotected state fluid path 404 can then be used for transporting (305) fluids to destination 411, which fluids can be aseptic or sterile fluids. Such transporting (305) of fluids can comprise filtering the fluid in the fluid path 404 using filter element 403 and the filtering can be sterile filtering. The terms "sterile" and "aseptic" are used interchangeably in this specification. The term "decontamination" as used herein denotes a process for removing or inactivating contamination, including without limitation viruses, bacteria, spores, prions, molds, yeasts, proteins, pyrogens and endotoxins, to acceptable levels. "Decontamination" as used herein includes both sterilization (that is, the destruction of all microorganisms, including bacterial spores to a probability of surviving organisms of typically less than $1:10^6$) and disinfection (that is, the destruction and removal of specific types of microorganisms).

Figure 2:
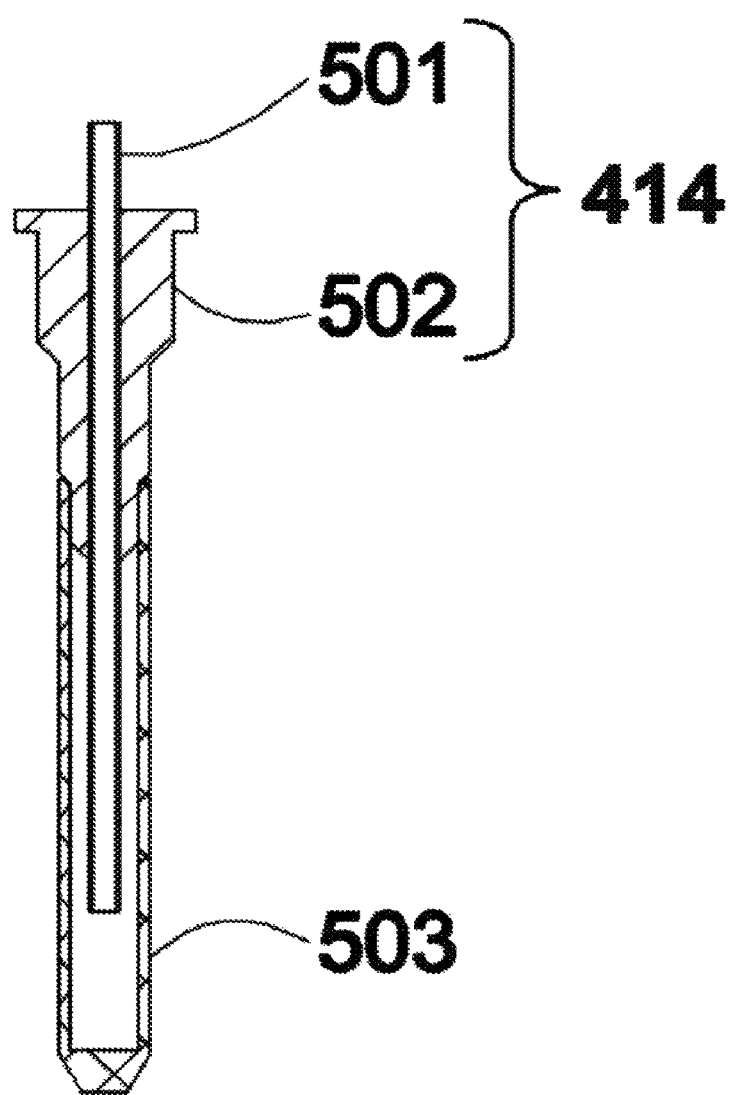
FIG. 2 shows detail of an end piece of an apparatus for the protecting and unprotecting of a fluid path in a controlled environment enclosure

In FIG. 2 a suitable arrangement for mechanically unprotecting (304) fluid path 404 is shown, comprising end piece 414 of fluid path 404 in the form of a fill needle, together with a fill needle sheath 503. The fill needle 414 comprises fill needle tubing 501 and fill needle hub 502. Fill needle tubing 501 is in fluid communication with fluid path 404 of FIG. 1 and is aseptically joined to fluid path 404. When the fluid path 404 is within controlled environment enclosure 420, the fill needle sheath 503 can be stored in a sheath removal station 413 of the controlled environment enclosure 420 shown in FIG. 1.

The fill needle hub 502 and the fill needle tubing 501 can be glued or welded together. In alternative embodiments the fill needle hub 502 and the fill needle tubing 501 can be made as one part out of solid material. The fill needle sheath 503 can be manufactured using materials with different thermal expansion coefficients to allow it to slide on and off the fill needle hub 502 after thermal expansion. Alternatively the fill needle sheath 503 can be designed to have a sliding fit on the fill needle hub 502 using porous PTFE or a steam permeable elastomeric material.

Protecting (301) the fluid path 404 comprises sealingly placing the fill needle sheath 503 over the fill needle 414 such that the fill needle sheath 503 seals with the needle hub 502. The fill needle sheath 503 and needle hub 502 can be equipped with one or multiple of tamper evident features 504 that will provide evidence of breaking the seal between needle hub 502 and fill needle sheath 503. Possible tamper evident features 504 include but are not limited to heat shrink bands, tape seals, breakable rings, tear-off connectors and snap connect tear-off connectors. Unprotecting (304) the fluid path 404 comprises removing the fill needle sheath 503 from the fill needle 414, thereby exposing the fill needle 414 to an environment within the controlled environment enclosure 420. When the fill needle 414 is in use within the controlled environment enclosure 420, the fill needle sheath 503 is stored in the sheath removal station 413.

Figure 3:
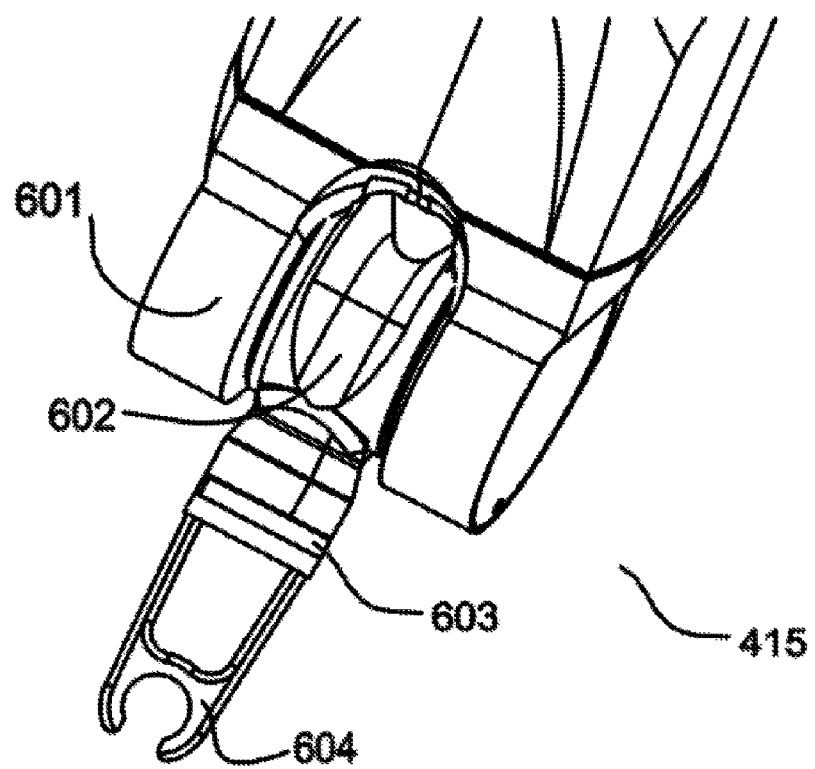
FIG. 3 shows detail of a robotic arm forming part of an apparatus for the protecting and unprotecting of a fluid path in a controlled environment enclosure

The mechanically unprotecting (304) the fill needle 414 when it is within controlled environment enclosure 420 can comprise using a robotic arm manipulation system 415 shown in FIG. 1. FIG. 3 illustrates part of the robotic arm manipulation system 415 of FIG. 1, wherein a forearm 601 is connected to a wrist 602, and the wrist 602 is connected to a tool flange 603. The end tool 604, shown in FIG. 3 as being fork shaped, has a partially opened bore of such diameter that the end tool 604 can slide around a narrow tubular section of needle hub 502 and the end tool 604 can move upwards to establish a precise locating fit to needle hub 502. For unprotecting (304) the fill needle 414, the end tool 604 moves the fill needle 414 with the fill needle sheath 503 and places the fill needle 414 with the fill needle sheath 503 in sheath removal station 413.

In one embodiment of the apparatus and method, the sheath removal station 413 heats the fill needle sheath 503, which thereby expands and releases its grip or seal to the needle hub 502. Practitioners in the field will appreciate that there are many different ways by which the fill needle sheath 503 can be removed from the fill needle 414. The end tool 604, through the motion of the robotic arm manipulation system 415, removes the fill needle 414 from the fill needle sheath 503. The fill needle sheath 503 can remain in the sheath removal station 413 while the robotic arm manipulation system 415 moves the fill needle 414 to the destination. In one embodiment of the apparatus and method the destination shown is the tray with vials 411 located on the pedestal 412 in FIG. 1.

The end tool 604 and the needle hub 502 can have various different other shapes allowing the use of various other closure systems such as, for example without limitation, a plug, a cap with sliding fit o-ring seal with minimal occluded surface area, a cap with membrane peel-off seal, or a twist-off cap. As understood by those skilled in the art, some closure systems will be more suitable than other closure systems for use with particular sterilization methods.

Materials of lesser permeability can be used in the manufacture of the flexible tubing 405, but this is not always an option. Tubing permeability can also be reduced by adding additional layers to the tubing. Example methods for establishing such additional layers around the flexible tubing 405 include, but are not limited to, heat shrinking with non-permeable polymers such as FEP, multilayer co-extrusion with non-permeable polymers, creating a diffusion barrier by polymeric coating such as poly(p-xylylene), encasing with layers of tape, and the fitting of a sleeve.

Figure 6:
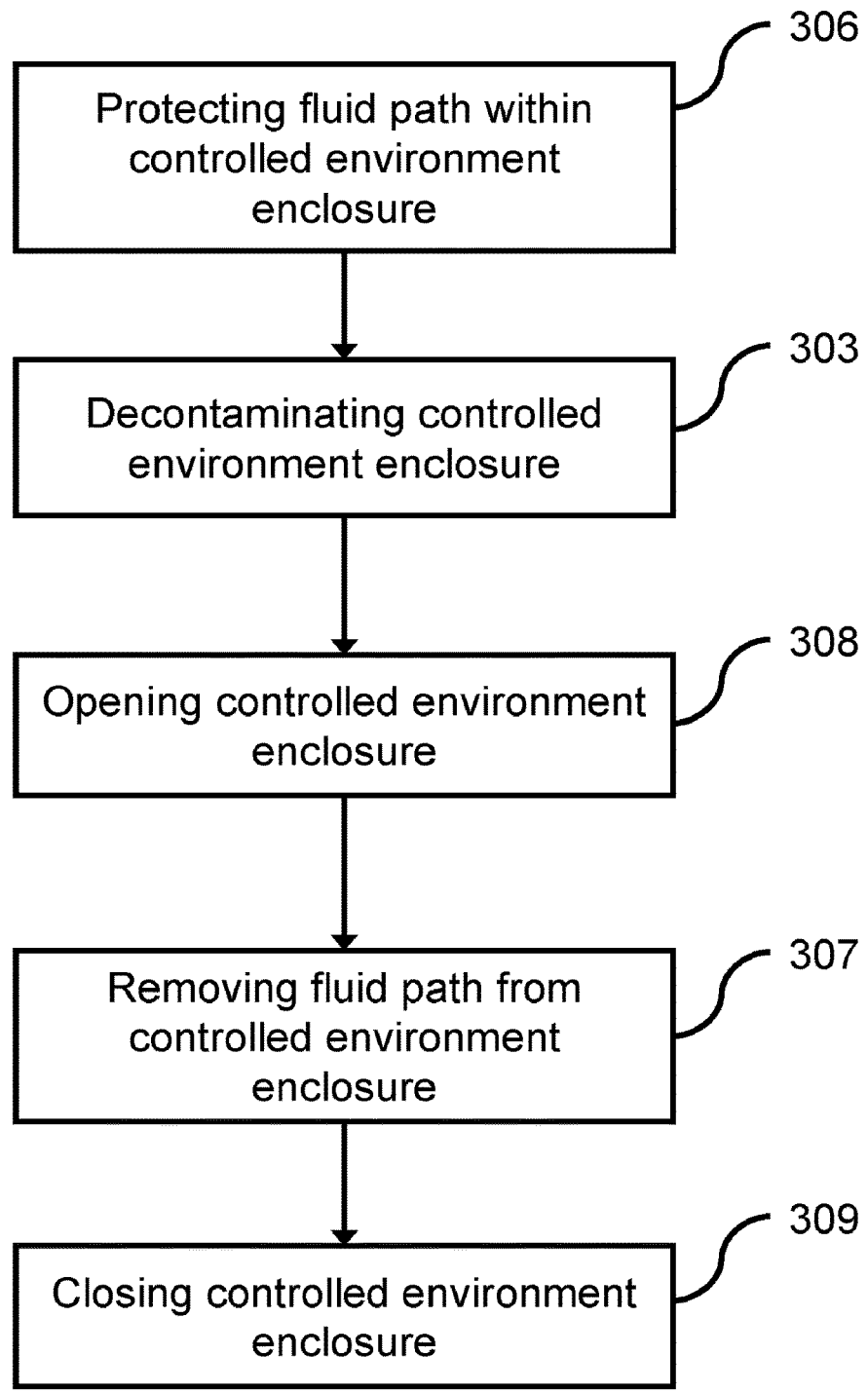
FIG. 6 shows a method flow chart of another aspect of the invention.

In a further aspect of the invention there is provided a method for uninstalling a fluid path 404 from the controlled environment enclosure 420. Referring to the apparatus of FIG. 1 and the flow chart of FIG. 6, the method comprises mechanically protecting (306) the fluid path 404 within the controlled environment enclosure 420 once the use of fluid path 404 has been completed, decontaminating (303) the controlled environment enclosure 420, and removing (307) the fluid path 404 from the controlled environment enclosure 420. The mechanically protecting (306) the fill needle 414 can comprise using the robotic arm manipulation system 415 shown in FIG. 1.

The mechanically protecting (306) the fill needle 414 within controlled environment enclosure 420 can comprise using the robotic arm manipulation system 415 of FIG. 1. The end tool 604 (See FIG. 3) of robotic arm manipulation system 415 is used to move the fill needle 414 to and place it in the fill needle sheath 503, which is housed in the sheath removal station 413. The sheath removal station 413 heats the fill needle sheath 503 until the fill needle sheath 503 can slide over fill needle 414 to suitably seal to needle hub 502 after cooling, to thereby protect (306) the fill needle 414 within controlled environment enclosure 420. The robotic arm manipulation system 415 can then further move the protected fluid path 404 as may be required.

In a further aspect of the invention the mechanically unprotecting (304) and the mechanically protecting (306) the fill needle 414 using the robotic arm manipulation system 415 can be done automatically. For example, a suitable controller 440 (see FIG. 1), communicating control instructions with the controlled environment enclosure 420 via a control line 450, can be programmed to automatically unprotect (304) the fill needle 414 using the robotic arm manipulation system 415 once the decontaminating (303) the controlled environment enclosure 420 has been completed. Such automation obviates human intervention in the step of mechanically unprotecting (304) the fill needle 414. In an embodiment of the method, the step of decontaminating (303) the controlled environment enclosure 420 can also be managed by controller 440. This allows the remainder of the steps of installing the fill needle 414, beyond the step of introducing (302) the fluid path 404 into the controlled environment enclosure 420, to be automated using controller 440, including the use of the fill needle for the purpose for which it is installed, and the mechanically protecting (306) the fill needle 414 after such use.

Figure 7:
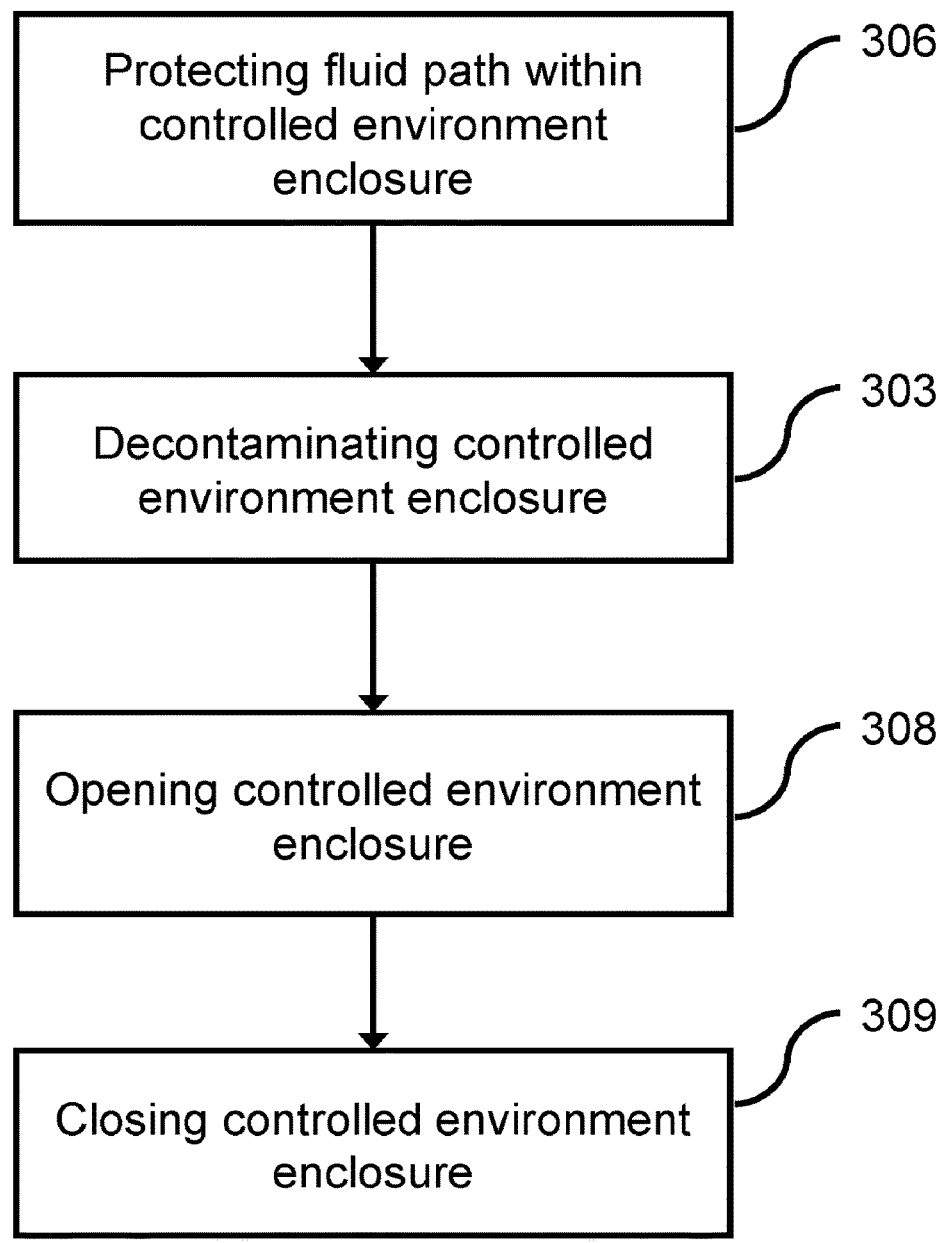
FIG. 7 shows a method flow chart of another aspect of the invention.
Figure 8:
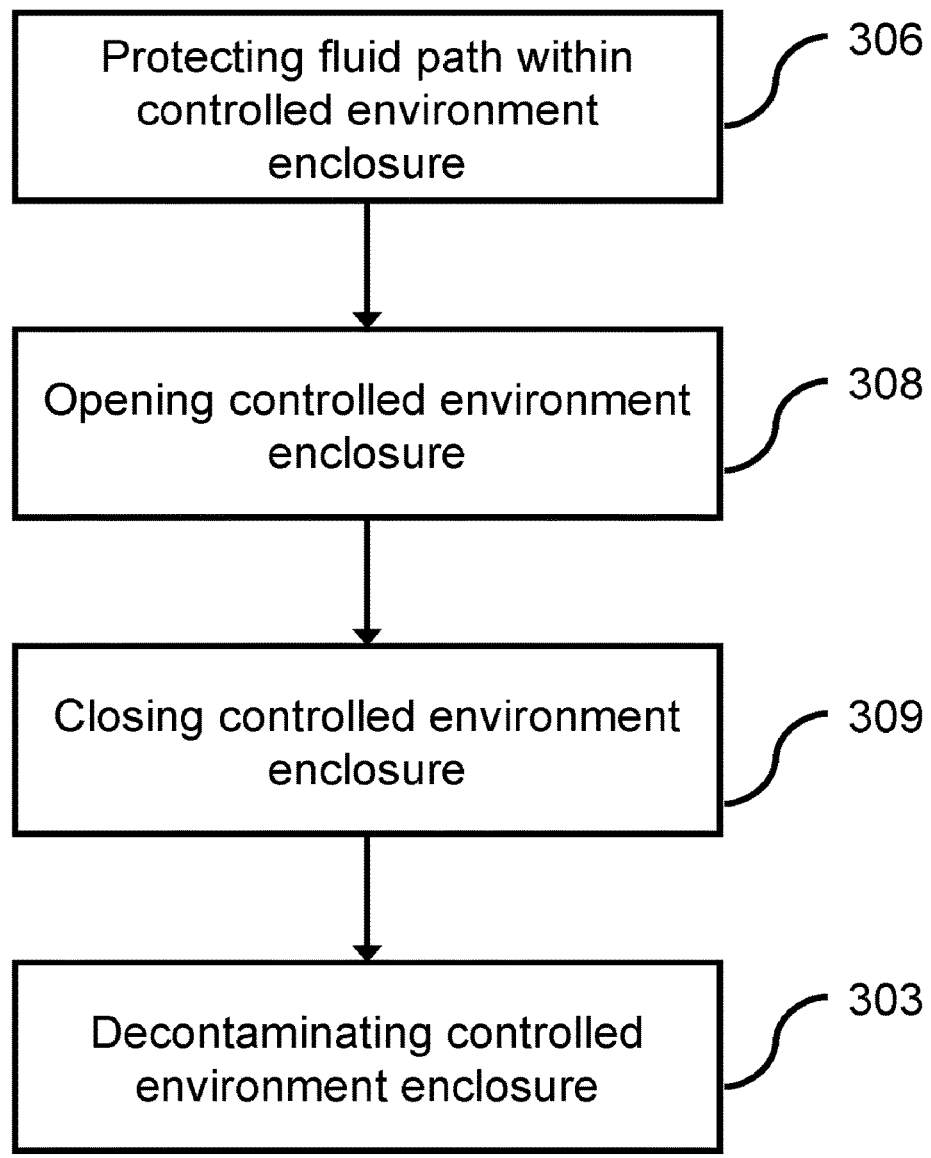
FIG. 8 shows a method flow chart of another aspect of the invention.

In a further aspect of the invention there is provided a method for decontaminating the controlled environment enclosure 420 having a fluid path 404. The method comprises mechanically protecting (306) the fluid path 404 within the controlled environment enclosure by sealingly placing the fill needle sheath 503 over the fill needle 414 such that the fill needle sheath 503 seals with the needle hub 502; decontaminating (303) the controlled environment enclosure 420; and opening (308) and closing (309) the controlled environment enclosure 420. The opening (308) and closing (309) the controlled environment enclosure 420 can be done after the decontaminating (303) the controlled environment enclosure 420, as may be the case when the fluid or the materials at the destination 411 are dangerous. This is shown in FIG. 7. Alternatively, the opening (308) and closing (309) the controlled environment enclosure 420 can be done before the decontaminating (303) the controlled environment enclosure 420. This is shown in FIG. 8, as may be the case when the external environment holds potential of contaminating the fluid or the materials at the destination 411. The mechanically protecting (306) the fill needle 414 can comprise using the robotic arm manipulation system 415 shown in FIG. 1, as already described.

The protecting (306) the fill needle 414 using the robotic arm manipulation system 415 can be done automatically via controller 440 (see FIG. 1). Controller 440 can be programmed for automatically mechanically protecting (306) the fill needle 414 using the robotic arm manipulation system 415, prior to opening (308) and closing (309) the controlled environment enclosure 420. The opening (308) and closing (309) the controlled environment enclosure 420 can likewise be automated via controller 440.

We have described thus far herein an embodiment of a sheath removal station 413 of FIG. 1 based on employing heat to secure or release fill needle 414 from fill needle sheath 503. We now turn to another embodiment of the subsystem comprising sheath removal station 413', fill needle 414', fill needle sheath 503', and robotic arm manipulation system 415 described at the hand of FIGS. 9a, 9b, 10 and 11. In this embodiment, we describe an alternative sheath removal system and associated sheath removal station 413', and provide more detail as regards fill needle 414', fill needle sheath 503', and robotic arm manipulation system 415.

Figure 9A:
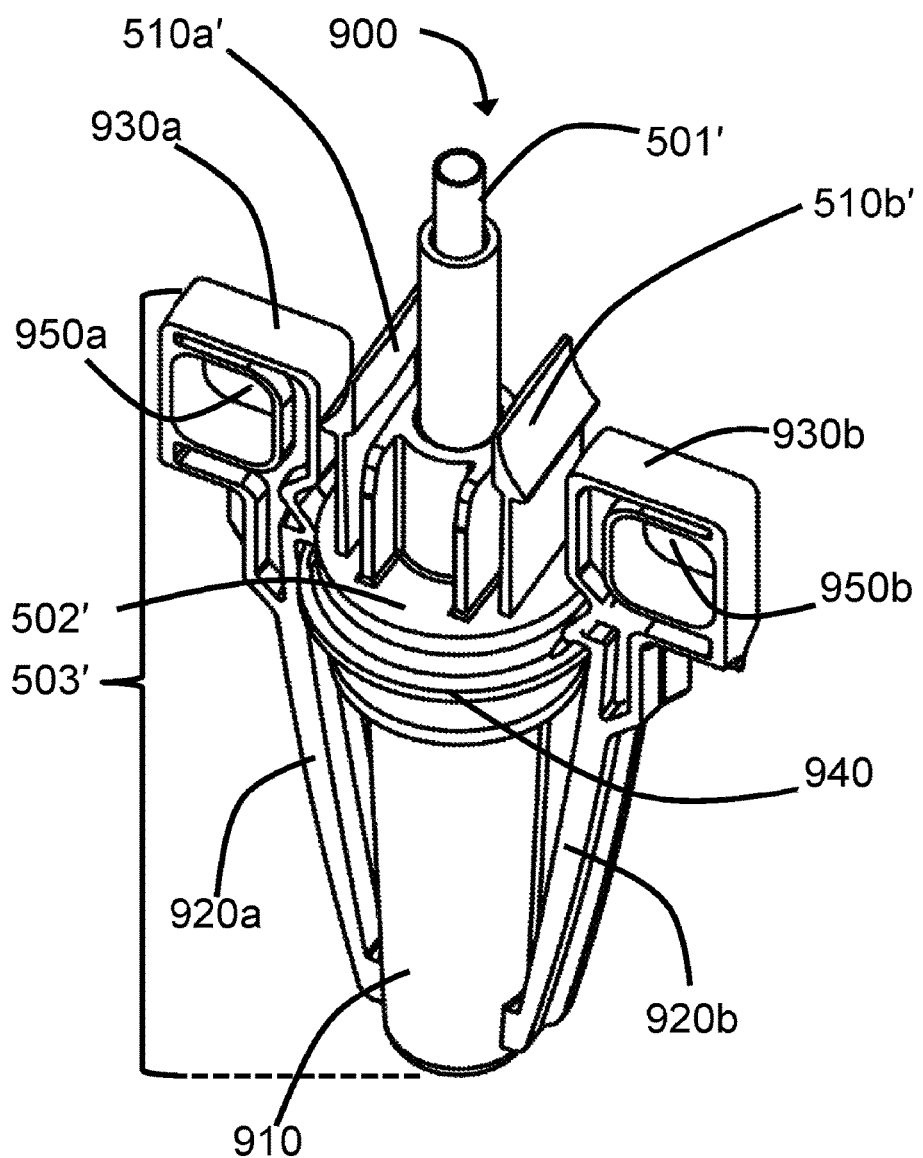
Figure 9B:
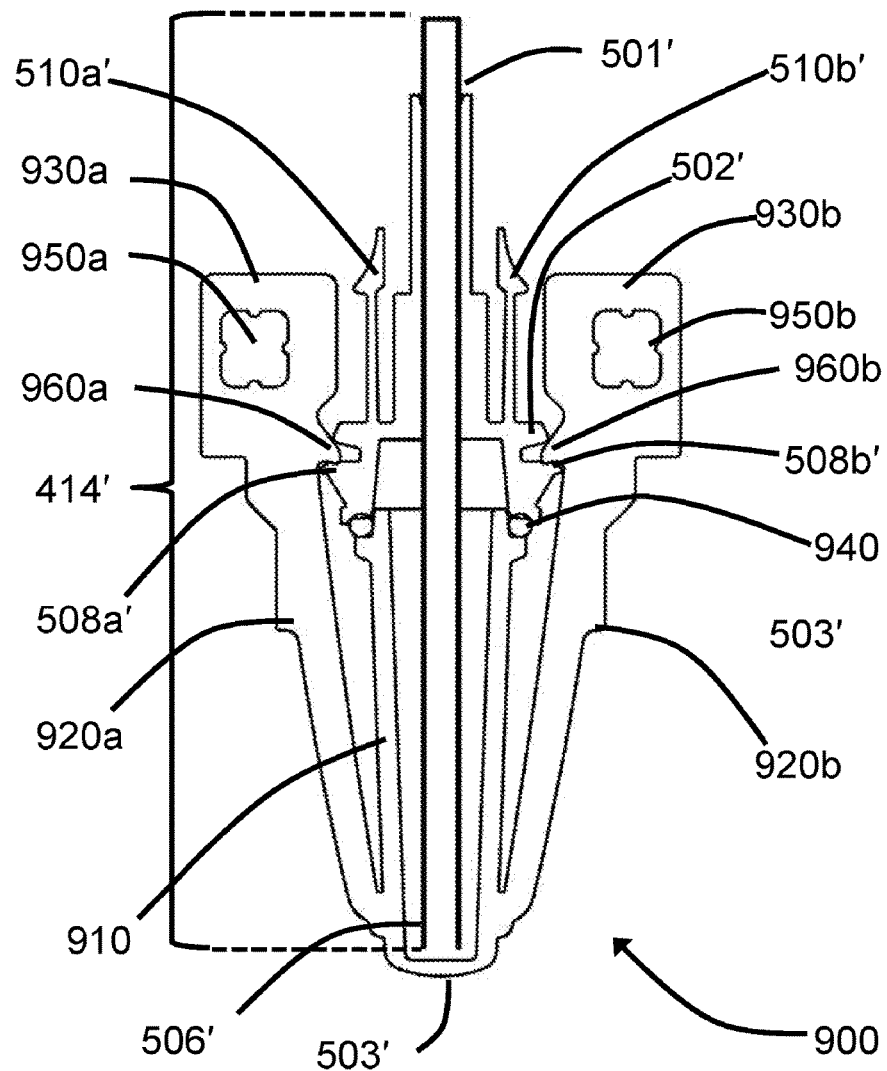

FIG. 9a and FIG. 9b provide isometric and sectional views respectively of the fill needle sheath 503' and fill needle 414' combination 900 of this embodiment. The term "aseptically sealed fill needle package" 900 will be used in the present specification to describe this combination of mutually aseptically sealed fill needle sheath 503' and fill needle 414'. While FIG. 9a provides perspective, the simplicity of FIG. 9b allows more elements to be clearly indicated and numbered. Fill needle sheath 503' comprises a substantially cylindrical vessel portion 910 configured to receive the dispensing end of fill needle 414', and two clamping members 930a and 930b attached to vessel portion 910 by spring loaded members 920a and 920b respectively. In one embodiment, shown in FIG. 9a and FIG. 9b, the spring loading is established by means of the natural elastic flexibility of members 920a and 920b. To this end, fill needle sheath 503' may be manufactured from a polymeric material with suitable inherent elasticity and that is compatible with aseptic systems requirements. Locating eyelets 950a and 950b are disposed in clamping members 930a and 930b respectively. Clamping members 930a and 930b further comprise clamping clips 960a and 960b respectively disposed to engage with filling needle 414' as described in more detail below.

Filling needle 414' may be configured in many different ways. In the present non-limiting exemplary embodiment, fill needle 414' comprises fill needle tubing 501' and fill needle hub 502'. Fill needle 414' comprises a dispensing portion 506', being the dispensing tip of fill needle 414'. Fill needle tubing 501' is in fluid communication with fluid path 404 of FIG. 1 and is aseptically joined to fluid path 404. Fill needle hub 502' mates axially face-to-face with fill needle sheath 503' in an aseptic pressure seal provided by elastically compressible O-ring 940. Fill needle hub 502' further comprises locating ledges 508a' and 508b' for engaging with clamping clips 960a and 960b of filling needle 414'. In manufacture, spring loaded members 920a and 920b are fashioned to be spring loaded when clamping clips 960a and 960b are engaged with locating ledge 508'. When filling needle 414' is sheathed in fill needle sheath 503' with compressible O-ring 940 under suitable compression, clamping clips 960a and 960b are engaged with locating ledge 508' and under a tension force directing clips 960a and 960b towards each other. Under these circumstances, the tension in fill needle sheath 503' is contained in spring loaded members 920a and 920b. Other embodiments for urging clips 960a and 960b towards each other when filling needle 414' is sheathed in fill needle sheath 503' are contemplated, including embodiments in which discrete springs are employed to render members 920a and 920b spring loaded.

Fill needle sheath 503' may be manufactured by injection molding of a suitable polymeric material. In order to keep units costs low it may specifically be injection molded as a single monolithic unit. In the present specification the term "monolithic" is employed to describe an object that is fashioned is a contiguous whole from one piece of material without joints or seams, whether by casting, molding, or deposition, or any other means. A single mold in the art of injection molding generally produces a monolithic product.

The locking member portions of fill needle hub 502' and the fill needle sheath 503' may in particular be integrally molded. This includes in particular spring loaded members 920a and 920b.

Figure 11:
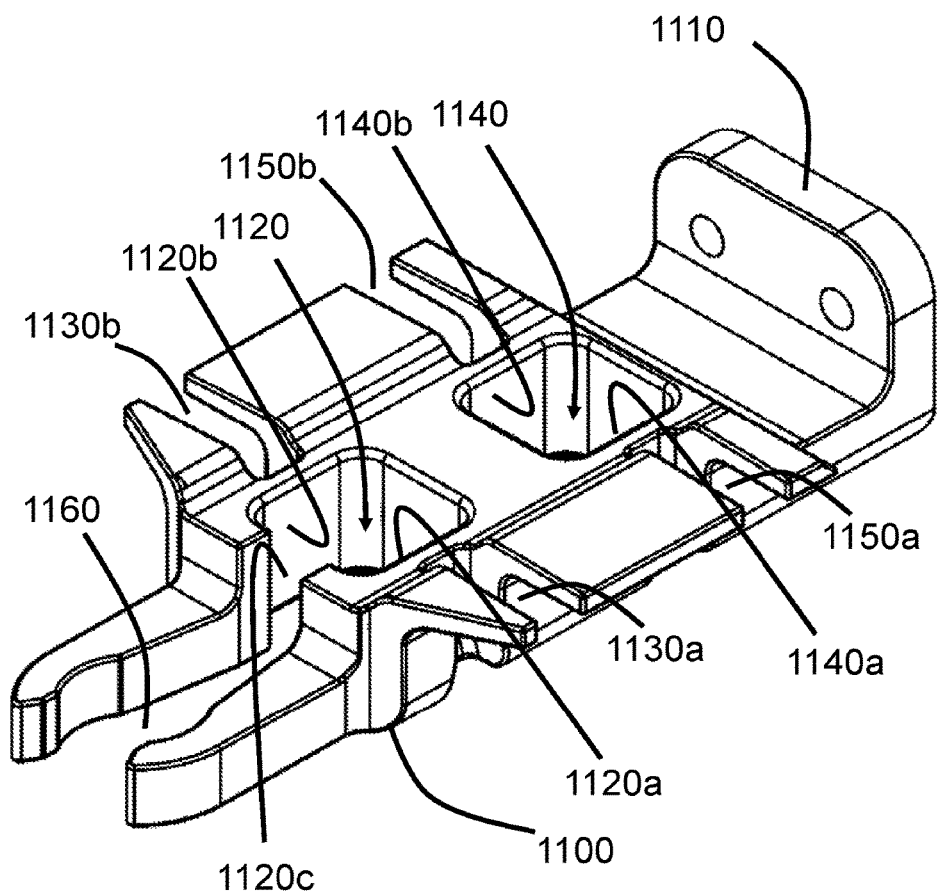
FIG. 11 shows a robotic arm end piece according to one embodiment of the invention for use with for use with the sheath removal station of FIG. 12 and the fill needle and fill needle sheath of FIG. 9a and FIG. 9b.

Fill needle hub 502' comprises two engagement clips 510a' and 510b' for engaging with robotic arm end piece 1100 of FIG. 11. The operation of these will be described below at the hand of FIG. 11. Engagement clips 510a' and 510b' are able to flex such that their top ends can be deflected closer together while engagement clips 510a' and 510b' can push back in reaction against whatever bodies are pushing them together. To this end engagement clips 510a' and 510b' may be spring loaded. In the embodiment of fill needle hub 502' shown in FIGS. 9a and 9b, engagement clips 510a' and 510b' are flexible by virtue of being manufactured from an elastic material such as, for example without limitation, a suitable polymeric material compatible with aseptic handling requirements. Engagement clips 510a' and 510b' are shaped to both clip over robotic arm end piece 1100 of FIG. 11 and be deflected toward each other by end piece 1100.

In the embodiment shown in FIG. 9a and FIG. 9b, fill needle hub 502' is shown as comprising several interior substructures. This approach allows the same mold to be employed for the manufacture by injection molding of all fill needle hubs, while the interior substructures are then adapted to differently sized fill needle tubing 501'. This allows costs to be kept low. Other arrangements of substructures are also contemplated, including without limitation embodiments wherein the entire fill needle hub 502' is one monolithic entity fashioned by injection molding of a suitable polymeric material compatible with aseptic requirements. Based on the above, fill needle package 900 comprises first and second sheath portions that together define a sealed cavity that aseptically encapsulates an implement portion when first and second locking mechanism portions are mutually mated.

In view of the above, flow path 404 of FIG. 1, as supplied for use in this embodiment, comprises flexible tubing 405, an aseptically sealing flange for aseptically sealing the flow path 404 to the controlled environment chamber 420, and aseptically sealed fill needle package 900.

Figure 9C:
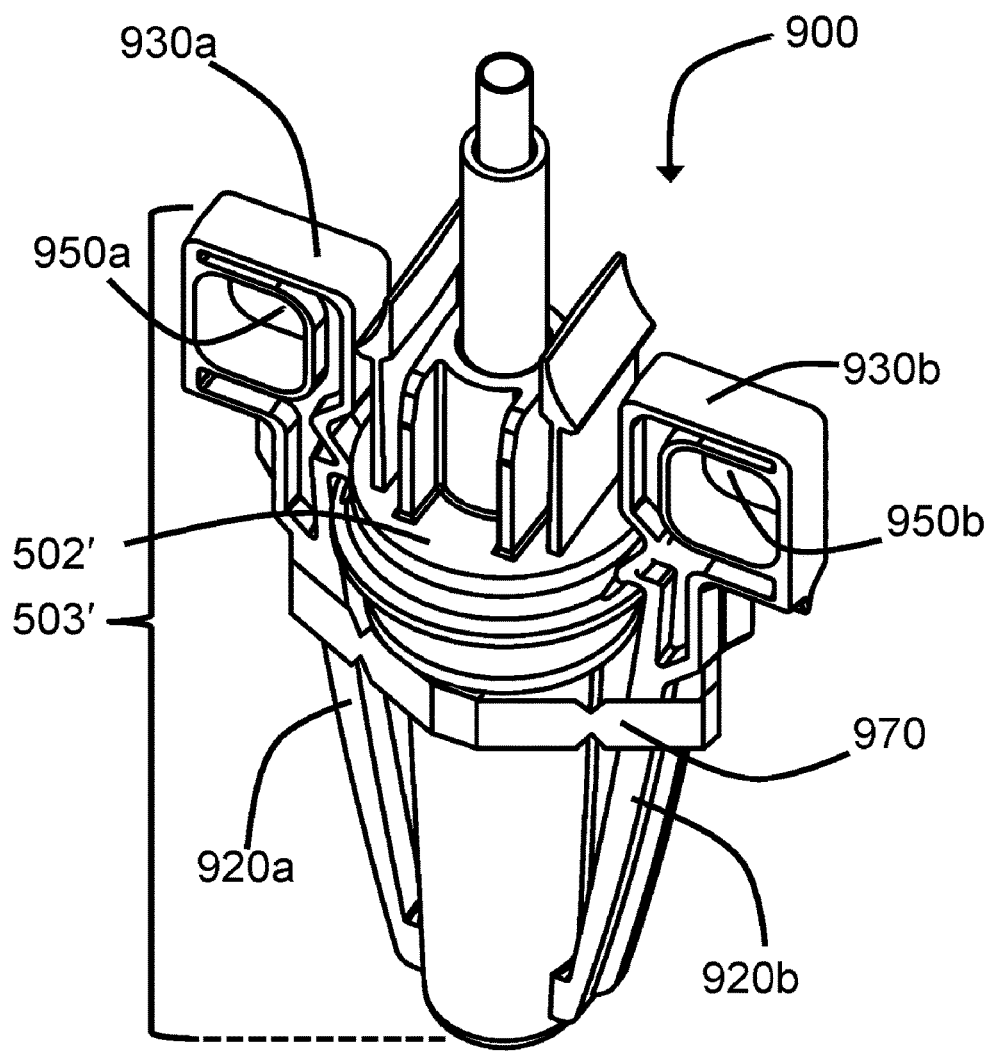
FIG. 9c shows the combination of a fill needle and a fill needle sheath with a tamper-indicator.

Turning now to FIG. 9c, aseptically sealed fill needle package 900 may have a tamper indicator 970 that is mechanically linked to one of the locking mechanism portions of fill needle package 900. In FIG. 9c tamper indicator 970 comprises a tearable strip across spring loaded members 920a and 920b. When locating eyelets 950a and 950b are forced apart, the portion of tamper indicator 970 disposed across spring loaded members 920a and 920b is torn irreversibly. Since the same act of separating locating eyelets 950a and 950b also leads to the separation of sealing surfaces between the fill needle hub 502' and the fill needle sheath 503', the breaking of tamper indicator 970 is a direct indicator of the breach of the aseptic seal between fill needle hub 502' and fill needle sheath 503'. The same tamper-evident arrangement may be made for the swab system described below.

Figure 10:
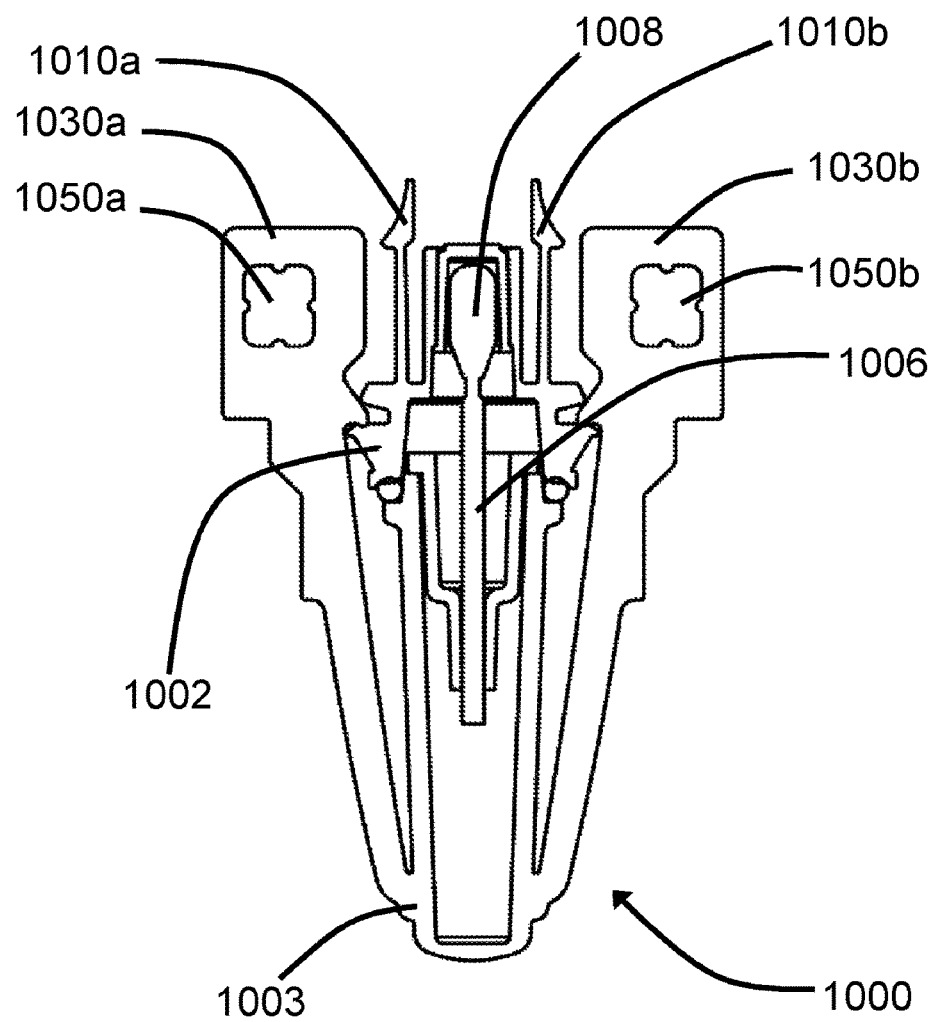
FIG. 10 shows a swab, swab sheath, and swab sheath cap for use with the sheath removal station of FIG. 12 and robotic arm end piece of FIG. 11.

As part of the process of filling a pharmaceutical container with a pharmaceutical product, a regulatory requirement may exist in some cases for the dispensing tip of the fill needle 414,414' to be swabbed with a suitable swab to collect potential contamination species. Such swabs are then typically evaluated by a suitably qualified laboratory in order to assess the aseptic state of the pharmaceutical dispensing process. To this end, in another aspect of the invention, an aseptically sealable/unsealable swab subsystem is provided. In FIG. 10, swab subsystem 1000 comprises a swab holder 1003 that may usefully be of the same design as fill needle sheath 503' of FIG. 9a and FIG. 9b. Swab 1006 is mounted within swab holder 1003 with the collection tip 1008 of swab 1006 protruding above the top of swab holder 1003. This arrangement allows the dispensing tip of the fill needle 414,414' to be swabbed by touching the dispensing tip to the collection tip 1008 of swab 1006. Swab holder 1003 may be a monolithic injection molded polymeric swab holder.

Swab subsystem 1000 further comprises a swab holder cap 1002 that may usefully be of the same design as fill needle hub 502' of FIG. 9a and FIG. 9b, with this modification that swab holder cap 1002 has no fill needle tube 502' and that swab holder cap 1002 is instead permanently sealed at the top. As regards all other mechanical operational aspects, fill needle sheath 503' and fill needle 414' combination 900 and swab subsystem 1000 may be identical. For this reason, the mechanical design aspects of swab subsystem 1000 will not be further discussed here. We shall, however, be referring below to engagement clips 1010a' and 1010b' of swab holder cap 1002 as regards their engagement with robotic arm end piece 1100 of FIG. 11. We shall also be referring below to locating eyelets 1050a and 1050b disposed in clamping members 1030a and 1030b respectively as regards their engagement with fingers. The term "aseptically sealed swab package" 1000 will be used in the present specification to describe this combination of mutually aseptically sealed swab holder cap 1002 and swab holder 1003 containing swab 1006. The swab 1006 is supplied for use packaged in the form of aseptically sealed swab package 1000. Based on the above, swab package 1000 comprises first and second sheath portions that together define a sealed cavity that aseptically encapsulates an implement portion when first and second locking mechanism portions are mutually mated. The locking member portions of f swab holder cap 1002 and the swab holder 1003 may in particular be integrally molded. This includes in particular spring loaded members of the structure.

FIG. 11 shows one embodiment of an endpiece 1100 for robotic arm 415 of FIG. 1 configured to engage with swab subsystem 1000 of FIG. 10 and with fill needle sheath 503' and fill needle 414' combination 900 of FIG. 9a and FIG. 9b. Flange 1110 is disposed and shaped for attaching endpiece 1100 to robotic arm 415 of FIG. 1. Openings 1120 and 1140 are disposed and shaped for holding fill needle 414' and swab holder cap 1004 respectively. In the case of fill needle 414', engagement clips 510a' and 510b' of fill needle hub 502' engage with end piece engagement surfaces 1120a and 1120b of endpiece 1100.

Procedurally, fill needle 414' is engaged as follows with endpiece 1100. Endpiece 1100 is moved forward over the part of fill needle tubing 501' that protrudes out of fill needle 414' and any associated section of flow path 404 joined to fill needle tubing 501' until opening 1120 is directly above fill needle 414'. In this process, opening 1120c allows endpiece 1100 to negotiate fill needle tubing 501'. Endpiece 1100 may then be lowered such that the bottom edges of engagement surfaces 1120a and 1120b engage with the sloped portions of engagement clips 510a' and 510b'. When endpiece 1100 is lowered further, engagement clips 510a' and 510b' are both flexibly deflected towards each other until engagement surfaces 1120a and 1120b pass the sloped portions of engagement clips 510a' and 510b' and engagement clips 510a' and 510b' snap back to engage their flat surfaces with engagement surfaces 1120a and 1120b of endpiece 1100. This securely locates fill needle 414' in endpiece 1100. When fill needle 414' is engaged with endpiece 1100, clamping members 930a and 930b are disposed in slots 1130a and 1130b respectively so as to render locating eyelets 950a and 950b accessible.

In the case of swab holder cap 1004, the engagement proceeds in the same fashion, except that there is no fill needle tubing 501' requiring an opening similar to 1120c. Endpiece 1100 is simply moved until opening 1140 is directly above swab holder cap 1004, after which endpiece 1100 is lowered such that the flat surfaces of engagement clips 1010a' and 1010b' engage with surfaces 1140a and 1140b of opening 1140 in a fashion similar to that described above for engagement clips 510a' and 510b'. When swab holder cap 1004 is engaged with endpiece 1100, clamping members 1030a and 1030b are disposed in slots 1150a and 1150b respectively so as to render locating eyelets 1050a and 1050b accessible.

When first using a fill needle 414, 414' and flow path 404, the product to be dispensed into containers is first run through the flow path 404 and fill needle 414, 414' to establish a steady and reliable flow. This initial volume of product may be dispensed into a priming bottle to be disposed of later. Grip 1160 on endpiece 1100 may be employed as a general tool for handling, for example, stoppers for such priming bottles and the like.

Figure 12:
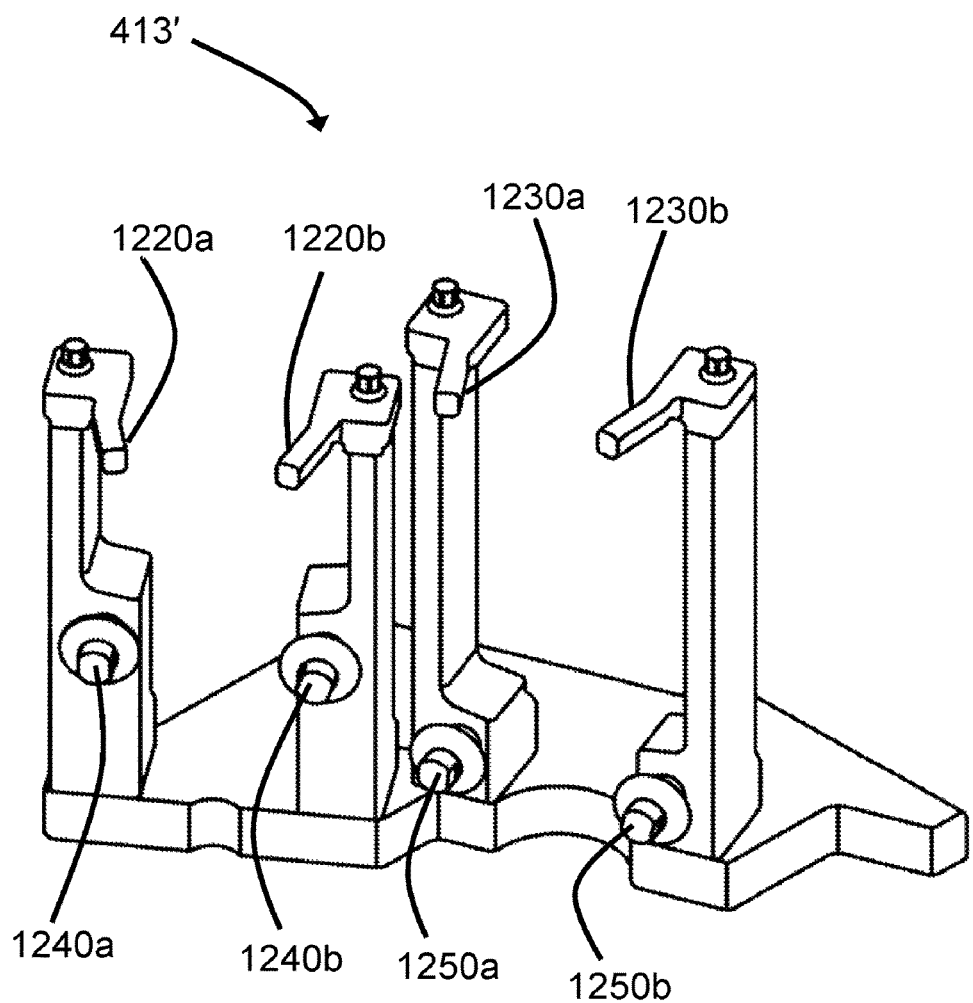
FIG. 12 shows a sheath removal station according to one embodiment of the invention.
Figure 13:
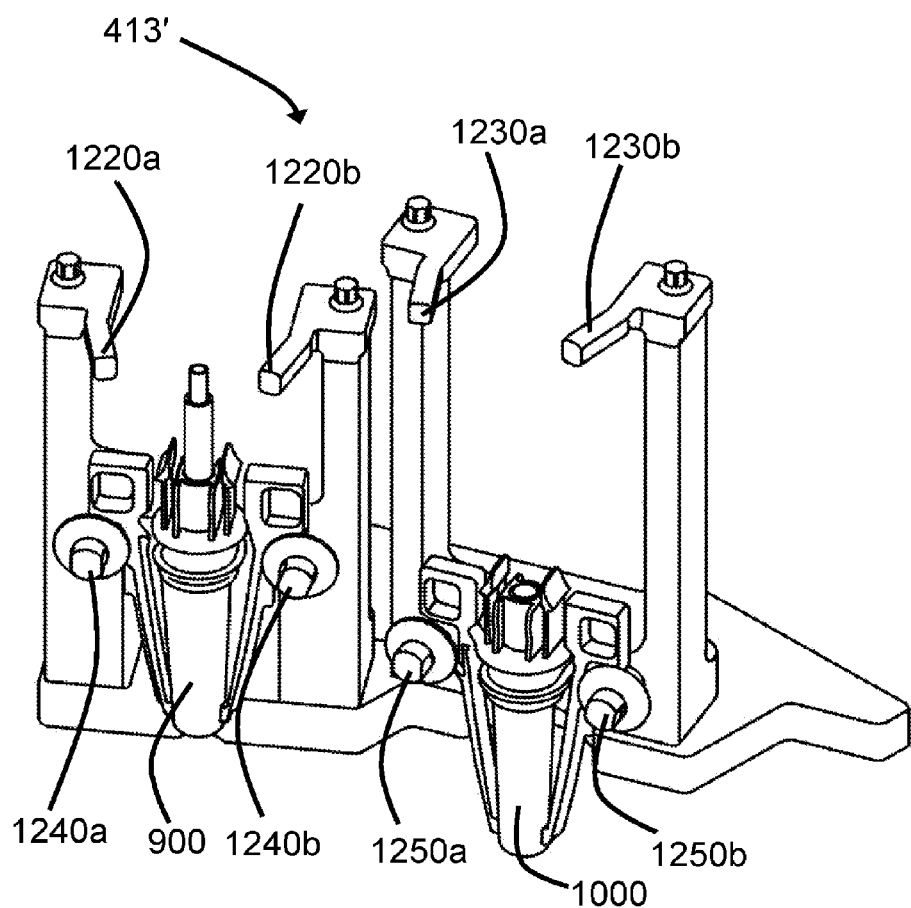
FIG. 13 shows the sheath removal station of FIG. 2 with a swab package and fill needle package suspended on the sheath removal station before use.

To describe the removal of fill needle sheath 503' from fill needle 414', we turn now to FIG. 12, in which sheath removal station 413' comprises sheath engagement fingers 1220a and 1220b for engaging with locating eyelets 950a and 950b of fill needle sheath 503'. When fill needle sheath 503', either with or without fill needle 414' engaged with it, is forced onto sheath engagement fingers 1220a and 1220b, the angled mutual orientation of sheath engagement fingers 1220a and 1220b forces apart clamping members 930a and 930b of fill needle sheath 503'. This action forces clamping clips 960a and 960b apart and disengages clamping clips 960a and 960b from locating ledge 508' of fill needle hub 502'. O-ring 940 thereby is allowed to expand to its uncompressed state and fill needle 414' is released from fill needle sheath 503'. Fill needle sheath 503' is therefore removably sealable to fill needle 414'. When not in use, fill needle sheath 503' is aseptically sealed to fill needle 414' and may be suspended from suspension stubs 1240a and 1240b as shown in FIG. 13. As will be described later, an operator may install flow path 404 in chamber 420. In that process, fill needle sheath 503' with fill needle 414' aseptically sealed to it, is positioned on suspension stubs 1240a and 1240b.

Sheath removal station 413' also comprises sheath engagement fingers 1230a and 1230b for engaging with locating eyelets 1050a and 1050b of swab holder 1003. When swab holder 1003, either with or without swab holder cap 1002 engaged with it, is forced onto sheath engagement fingers 1230a and 1230b, the angled mutual orientation of sheath engagement fingers 1230a and 1230b forces apart clamping members 1030a and 1030b of swab holder 1003. This action disengages swab holder cap 1002 from swab holder 1003. Swab holder 1003 is therefore removably sealable to swab holder cap 1002. When not in use, swab holder 1003 aseptically sealed to swab holder cap 1002 may be suspended from suspension stubs 1250a and 1250b as shown in FIG. 13. As will be described later, at the start of the process of filling pharmaceutical containers with pharmaceuticals in chamber 420, an operator may install swab holder 1003 aseptically sealed to swab holder cap 1002 on suspension stubs 1250a and 1250b as per FIG. 13.

Figure 14A:
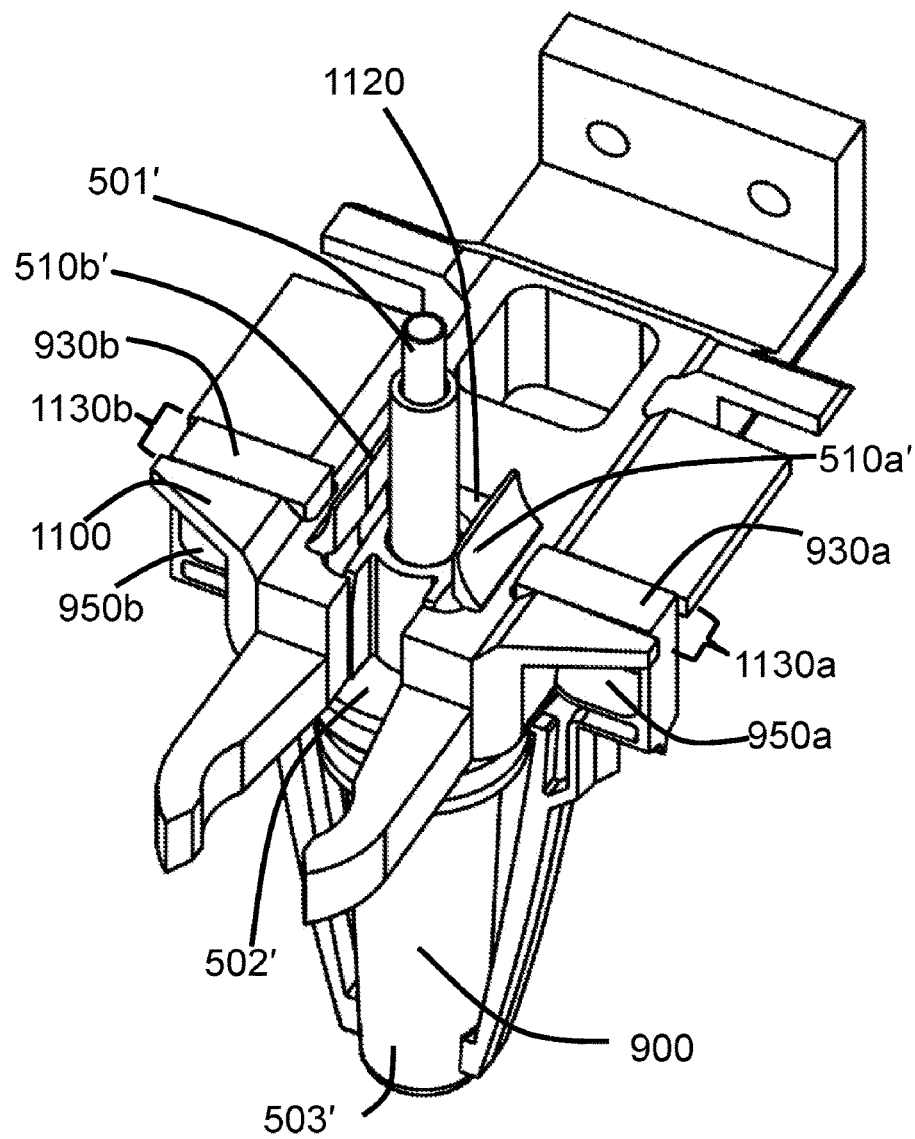
FIG. 14a shows the fill needle package of FIG. 9a and FIG. 9b held by the robotic arm end piece of FIG. 11.
Figure 14B:
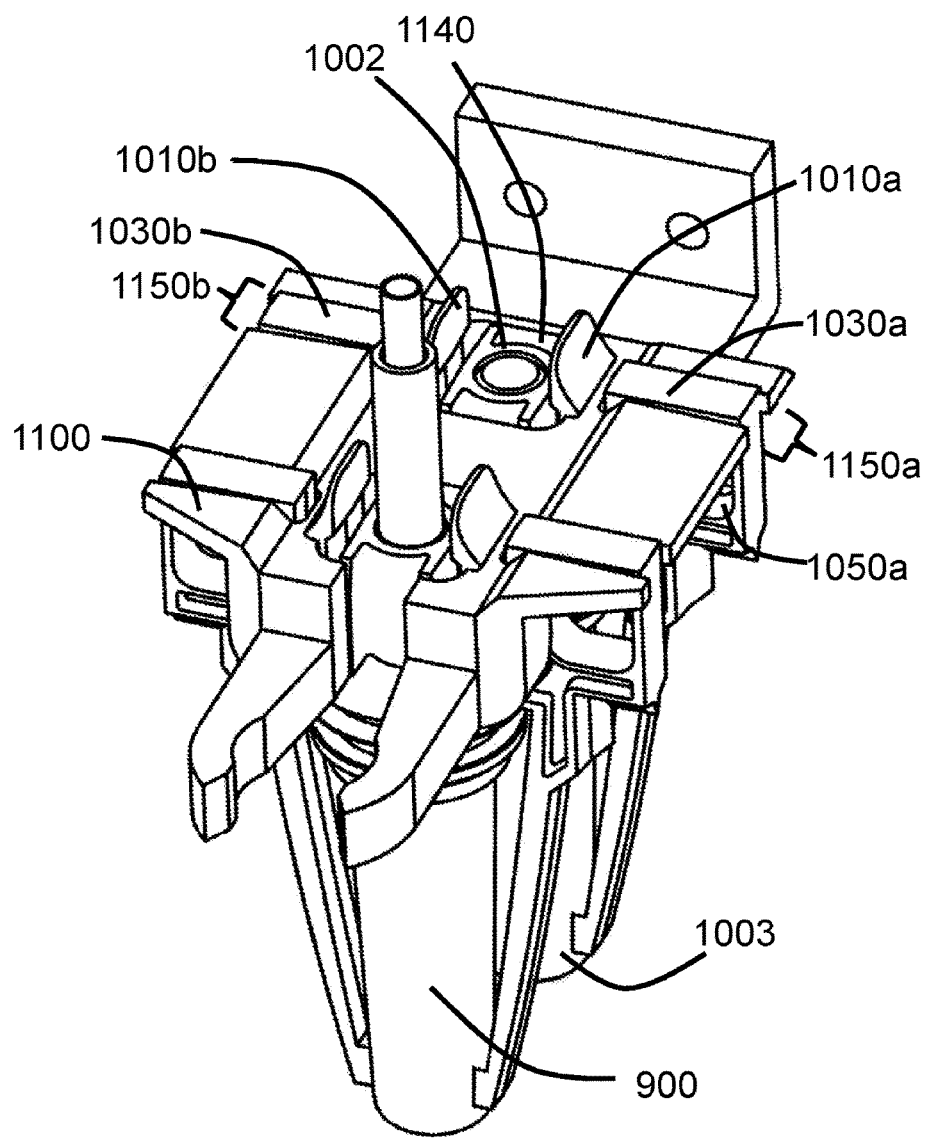
FIG. 14b shows the fill needle package of FIG. 9a and FIG. 9b as well as the swab package of FIG. 10 held by the robotic arm end piece of FIG. 11.

FIG. 14a shows robotic arm endpiece 1100 holding aseptically sealed fill needle package 900 by engagement clips 510a' and 510b' of fill needle hub 502'. FIG. 14b shows robotic arm endpiece 1100 holding aseptically sealed swab package 1000 by engagement clips 1010a and 1010b of swab cap 1002.

In operation, fluid path 404 is sealed aseptically to controlled environment enclosure 420 and fill needle package 900 is suspended on suspension stubs 1240a and 1240b of sheath removal station 413' as shown in FIG. 13. Swab package 1000 is introduced into enclosure 420 and suspended on stubs 1250a and 1250b of sheath removal station 413' as shown in FIG. 13. Controlled environment enclosure 420 may now be decontaminated using any of the various means previously described. Fluid path may now be unprotected by unsealing fill needle 414' fill needle sheath 503'. This may be done using robotic arm 415 as explained above at the hand of FIG. 12. This step leaves fill needle sheath 503' located on sheath engagement fingers 1220a and 1220b and fill needle 414' located on robotic arm endpiece 1100.

Swab holder cap 1002 may be similarly removed from swab holder 1003 to expose swab 1006 to the environment in enclosure 420. The process leaves swab holder 1003 with swab 2006 located on sheath engagement fingers 1230a and 1230b of sheath removal station 413'. Robotic arm 415 now may proceed to fill pharmaceutical vials 411 located on pedestal 412 in FIG. 1 with fluid via fill needle 414'. Fill needle 414' and swab holder cap 1002 remain resident on robotic arm endpiece 1100 during the filling process.

When filling has been completed, robotic arm 415 automatically moves robotic arm endpiece 1100 with fill needle 414' and swab holder cap 1002 to sheath removal station 413' to touch the dispensing end 506' of fill needle 414' to the exposed tip 1008 of swab 1006.

Using robotic arm 415, eyelets 950a and 950b of fill needle sheath 503' are engaged with sheath engagement fingers 1220a and 1220b to allow fill needle 414' to be aseptically sealed to fill needle sheath 503', thereby protecting the fluid path 404. Eyelets 1050a and 1050b of swab holder 1003 may similarly engage with sheath engagement fingers 1230a and 1230b of sheath removal station 413' to allow swab holder 1003 and swab holder cap 1002 to be sealed aseptically to each other, thereby protecting the swab 2006. Fluid path 404 and sealed swab package 1000 may now be removed from controlled environment enclosure 420.

As shown in FIG. 14b, robotic arm endpiece 1100 has no moving parts and is capable of simultaneously bearing both fill needle package 900 and swab package 1000. Despite both robotic arm endpiece 1100 and sheath removal station 413' having no moving parts, they are jointly capable of opening and closing both fill needle package 900 and swab package 1000. This is possible by virtue of the interaction between the engagement fingers 1220a, 1220b, 1230a, 1230b of sheath removal station 413' and the eyelets 950a and 950b of fill needle sheath 503' and eyelets 1050a and 1050b of swab holder 1003, combined with the spring-loaded or flexible nature of portions of fill needle sheath 503' and swab holder 1003.

Figure 15:
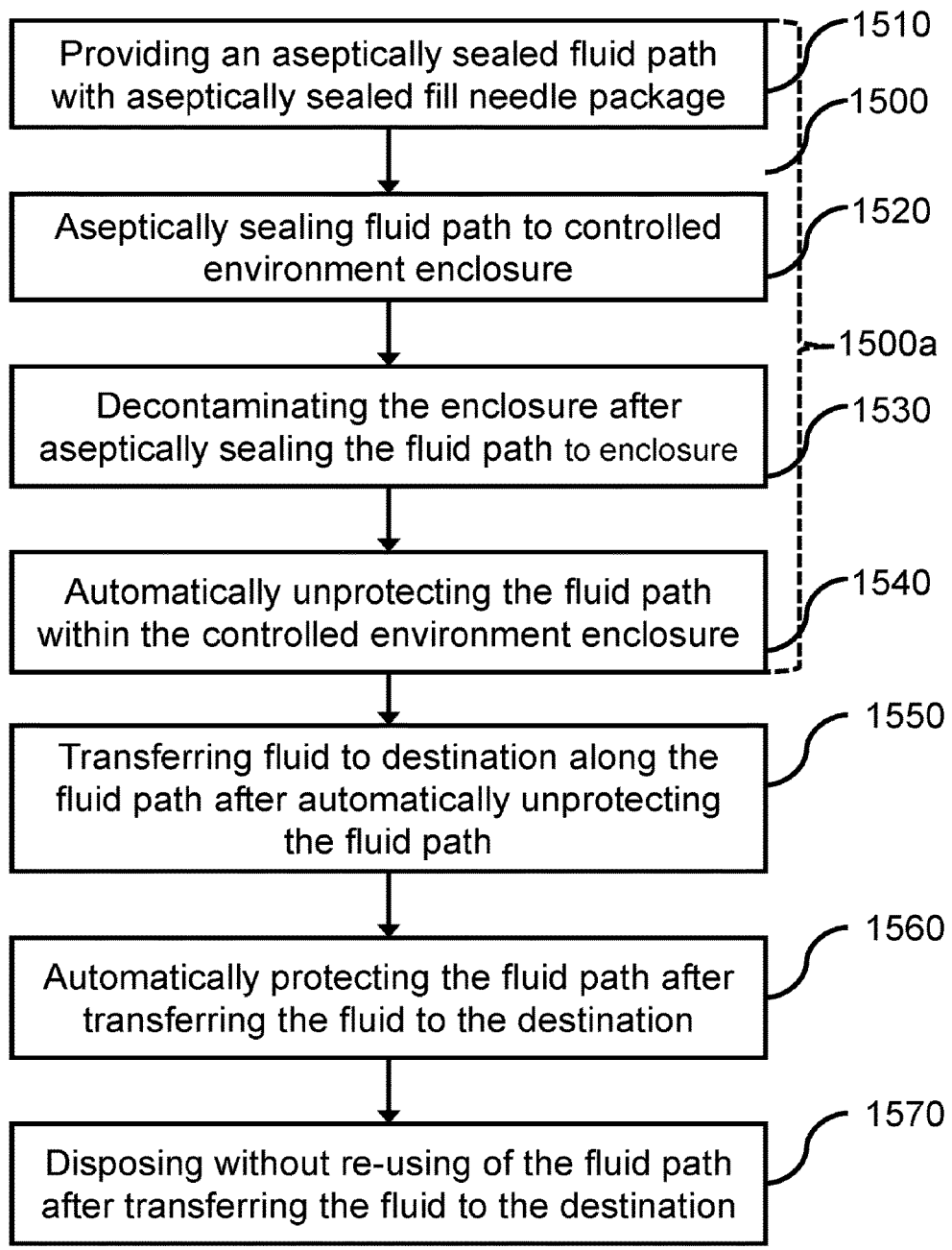
FIG. 15 shows a flow chart of (a) method for transferring within a controlled environment enclosure a fluid along a fluid path to a destination within the controlled environment enclosure and (b) a method for installing a fluid path in the controlled environment enclosure.

In one aspect of the invention, described at the hand of FIG. 15, a method is provided for transferring (1500) within a controlled environment enclosure a fluid along a fluid path to a destination within the controlled environment enclosure, the method comprising providing (1510) an aseptically sealed fluid path comprising an aseptically sealed fill needle package, aseptically sealing (1520) the fluid path to the controlled environment enclosure, decontaminating (1530) the controlled environment enclosure after aseptically sealing the fluid path to the controlled environment enclosure, automatically unprotecting (1540) the fluid path within the controlled environment enclosure, transferring (1550) the fluid to the destination along the fluid path after the automatically unprotecting, and disposing without re-using (1570) of the fluid path after transferring the fluid to the destination.

The automatically unprotecting (1540) may be by automatically operating a robotic arm. The decontaminating (1530) the controlled environment enclosure may automatically be done after the sealing the fluid path to the controlled environment enclosure. The providing an aseptically sealed fluid path (1510) may comprise providing a fill needle removably and aseptically sealed to a fill needle sheath and the sheath may be a monolithic injection molded polymeric fill needle sheath. The providing an aseptically sealed fluid path (1510) may comprise providing a pre-sterilized tube aseptically sealed to the fill needle. The transferring (1550) the fluid to a destination may comprise transferring the fluid to at least one of a culture of cells, a culture of tissue, an enzyme solution, a suspension of immobilized enzymes, a mix of active ingredients, and an excipient. The transferring (1550) the fluid may be transferring an aseptic fluid. The transferring (1550) within a controlled environment enclosure may be transferring within an isolator. The transferring the fluid (1550) to a destination may comprise at least one of transferring the fluid to microwell plates and to containers for pharmaceutical products.

The method may further comprise automatically protecting (1560) the fluid path after transferring the fluid to the destination and before disposing of the fluid path. The transferring (1550) the fluid may comprise filtering the fluid in the fluid path. The filtering may be sterile filtering.

As part of the method described above, a method (1500a) is provided for installing a fluid path within a controlled environment enclosure comprising, providing (1510) an aseptically sealed fluid path comprising an aseptically sealed fill needle package, aseptically sealing (1520) the fluid path to the controlled environment enclosure, decontaminating (1530) the controlled environment enclosure after aseptically sealing the fluid path to the controlled environment enclosure, and automatically unprotecting (1540) the fluid path within the controlled environment enclosure. The automatically unprotecting may be by automatically operating a robotic arm. The decontaminating the controlled environment enclosure may be automatically done after the sealing the fluid path to the controlled environment enclosure. The providing a fill needle may comprise providing a fill needle removably and aseptically sealed to a fill needle sheath. The providing a fill needle may comprise providing a fill needle removably and aseptically sealed to a monolithic injection molded polymeric fill needle sheath.

Figure 16:
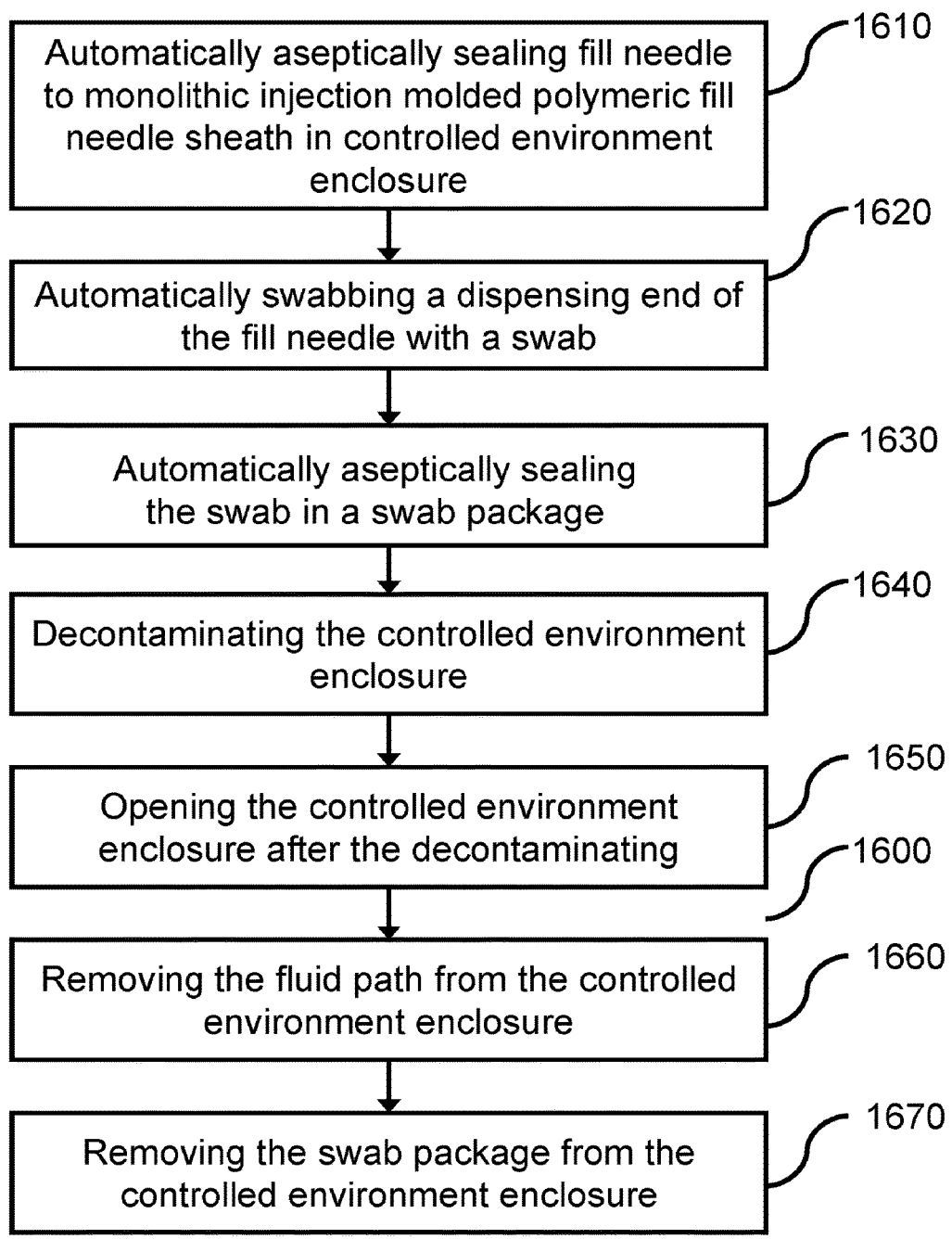
FIG. 16 shows a flowchart of a method for uninstalling from a controlled environment enclosure a fluid path comprising a fill needle.

In a further aspect of the invention described at the hand of FIG. 16, a method is provided for uninstalling (1600) from a controlled environment enclosure a fluid path comprising a fill needle, the method comprising automatically aseptically sealing (1610) the fill needle to a monolithic injection moulded polymeric fill needle sheath within the controlled environment enclosure, decontaminating (1640) the controlled environment enclosure after aseptically sealing (1610) the fluid path, opening (1650) the controlled environment enclosure after the decontaminating (1640), and removing (1660) the fluid path from the controlled environment enclosure. The method may further comprise automatically swabbing (1620) a dispensing end of the fill needle with a swab and automatically aseptically sealing the swab (1630) in a swab package before decontaminating (1640) the controlled environment, and removing (1670) the swab package from the controlled environment enclosure after opening the controlled environment enclosure.

The automatically aseptically sealing the fluid path (1610) may be by automatically operating a robotic arm. The decontaminating (1640) the controlled environment enclosure may be done automatically after the sealing (1610) the fluid path. The opening (1650) the controlled environment enclosure is done automatically after the decontaminating (1640) the controlled environment enclosure. The automatically swabbing (1620) may be by automatically operating a robotic arm. The automatically aseptically sealing (1610) the fluid path may be by automatically operating the robotic arm. The decontaminating (1640) the controlled environment enclosure may be done automatically after the sealing the fluid path (1610) and sealing the swab (1630). The swabbing (1620) may be with a swab disposed in a monolithic injection molded polymeric swab holder.

As part of the above methods, a subsidiary method is provided for decontaminating a controlled environment enclosure containing a fluid path having a fill needle, the method comprising automatically aseptically sealing (1610) the fill needle to a monolithic injection molded polymeric fill needle sheath within the controlled environment enclosure, and decontaminating (1620) the controlled environment enclosure after aseptically sealing (1610) the fluid path. The automatically aseptically sealing (1610) the fluid path may be by automatically operating a robotic arm. A subsidiary method is also provided for decontaminating a controlled environment enclosure containing a swab disposed in a swab holder, the method comprising automatically aseptically sealing the swab holder to a swab holder cap (1630) within the controlled environment enclosure, and decontaminating (1640) the controlled environment enclosure after aseptically sealing the swab holder to a swab holder cap. The automatically aseptically sealing (1630) the swab holder to a swab holder cap may be by automatically operating a robotic arm.

In the above-described embodiments, a pair of injection-molded parts are snapped together using integrally molded leaf spring members with clamping clips that engage with locating ledges. This action provides a positive mechanical detent that ensures that the implement is reliably sealed inside the sheath. But one of ordinary skill in the art would recognize that a variety of other types of mechanisms can be used to provide this type of action, including but not limited to cam-based mechanisms, ratcheting mechanisms, bistable linkages, spring-loaded balls, snaps, and latch pins.

The mechanisms in the above-described embodiments are presented in configurations that allow a concave sheath and cover-like hub to be engaged with each other along a vertical axis, but other geometric configurations can also be implemented. A pair of concave sheath portions could both partly enclose an implement in a downward-facing clamshell-type configuration, for example. And while the sheath and its corresponding hub are preferably manufactured as two completely separate parts as described above, they could also be built as a compound unit, such as by connecting them with a hinge or tether.

The above-described embodiments also provide bearing surfaces on engagement clips and in eyelets that respectively interact with an endpiece on a robot arm and protrusions on a holding station, which allow a robot arm to automatically open and close the sheath. But one of ordinary skill in the art would recognize that many other combinations and arrangements of bearing surfaces could also be employed.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a tangible computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A fluid handling assembly for automatically carrying out a fluid handling process in an aseptic environment, the fluid handling assembly disposed in a controlled environment enclosure configured to aseptically isolate the process and hold the fluid handling assembly, further disposed with a robot arm disposed within the enclosure to manipulate the fluid handling assembly, the fluid handling assembly comprising:
    an implement portion for conveying fluid in the fluid handling process;
    a first sheath portion, the implement portion disposed within the first sheath portion, the first sheath portion including:
        a first locking mechanism portion, and
        a first sealing portion,
    a second sheath portion including:
        a second locking mechanism portion configured to mate with the first locking mechanism portion, and
        a second sealing portion disposed to aseptically seal with the first sealing portion when the first and second locking mechanism portions are mutually mated, and
    wherein the first and second sheath portions define a sealed cavity that aseptically encapsulates the implement portion when the first and second locking mechanism portions are mutually mated.

2. The assembly of claim 1 wherein the assembly is a fill assembly and the implement portion comprises a proximal dispensing portion of a fill needle, the fill needle including a fluid conduit that extends through the first sheath portion to a distal fluid supply end so that, when the first and second locking mechanism portions are mutually mated, the proximal dispensing portion of the fill needle is located inside the cavity and the distal fluid supply end of the fluid conduit is located outside the cavity.

3. The assembly of claim 2 wherein the fluid conduit includes a flexible tube in fluid communication with the proximal dispensing portion of the fill needle.

4. The assembly of claim 1 wherein the assembly is a swab assembly and the implement portion comprises a swab disposed inside the cavity when the first and second locking mechanism portions are mutually mated.

5. The assembly of claim 1 further comprising:
    an articulated arm associated with the robot arm disposed within the enclosure to manipulate the fluid handling assembly.

6. The assembly of claim 5 wherein the first and second sheath portions respectively comprise first and second engagement portions.

7. The assembly of claim 6 further comprising:
    a robotic arm endpiece for the robotic arm, the endpiece configured to bear the first sheath portion by engagement with positive detent with the first engagement portion; and
    a holding station comprising a first holding fixture to hold the second sheath portion, the fixture configured for engaging with the second engagement portion.

8. The assembly of claim 7 wherein the holding fixture comprises angled fingers disposed to engage with the second engagement portion of the second sheath portion to release the first sheath portion from the second sheath portion.

9. The assembly of claim 8 wherein the holding station comprises a second holding fixture configured to suspend the mutually engaged first and second sheath portions.

10. The assembly of claim 1 wherein the first and second sheath portions are separate injection molded parts and wherein the locking mechanism portions include at least one integrally molded spring member.

11. The assembly of claim 10 further including a tamper indicator that is mechanically linked to one of the locking mechanism portions and includes a portion that is constructed to irreversibly tear in response to the mechanical separation of the first and second sealing surfaces.

12. The assembly of claim 1 wherein:
   the first and second locking mechanism portions are configured to mutually mate when the first and second locking mechanism portions are moved towards each other along a locking axis,
   the first sheath portion further includes a first bearing surface positioned at least generally normal to the locking axis, and
   the second sheath portion further includes a second bearing surface positioned at least generally normal to the locking axis and facing the first bearing surface.

* * * * *